US012605392B1

(12) United States Patent
Sachdeva et al.

(10) Patent No.: US 12,605,392 B1
(45) Date of Patent: Apr. 21, 2026

(54) CANNABINOID COMPOSITION AND METHOD OF TREATING DIABETIC AND CHEMOTHERAPY INDUCED NEUROPATHIC PAIN

(71) Applicant: Florida A&M University, Tallahassee, FL (US)

(72) Inventors: Mandip Sachdeva, Tallahassee, FL (US); Anil Kumar Kalvala, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 17/844,157

(22) Filed: Jun. 20, 2022

Related U.S. Application Data

(60) Provisional application No. 63/212,238, filed on Jun. 18, 2021.

(51) Int. Cl.
| | |
|---|---|
| *A61K 31/05* | (2006.01) |
| *A61K 9/127* | (2006.01) |
| *A61K 35/51* | (2015.01) |
| *A61K 36/185* | (2006.01) |
| *A61P 25/04* | (2006.01) |

(52) U.S. Cl.
CPC .............. *A61K 31/05* (2013.01); *A61K 9/127* (2013.01); *A61K 35/51* (2013.01); *A61K 36/3482* (2024.05); *A61P 25/04* (2018.01)

(58) Field of Classification Search
CPC ..................................................... A61K 31/05
See application file for complete search history.

(56) References Cited

U.S. PATENT DOCUMENTS

2019/0297882 A1 * 10/2019 Aeschbach .............. C11D 3/48
2021/0260201 A1 * 8/2021 Chukly .................. A61K 47/64

FOREIGN PATENT DOCUMENTS

WO WO-2021181399 A1 * 9/2021 ............. A61K 31/05
WO WO-2022067223 A2 * 3/2022 ............. A61K 31/05

OTHER PUBLICATIONS

Fairaq et al. Medico-Legal Update, Jan.-Mar. 2021, vol. 21, pp. 119-123 (Year: 2021).*
Anil et al. Nature: Scientific Reports 2021, 11, 1462, pp. 1-14 (Year: 2021).*
Paland et al. Frontiers in Immunology, Feb. 2021, 12, Article 631233, pp. 1-13 (Year: 2021).*
Mulcahy et al. (Journal of Extracellular Vesicles 2014, 3, 24641 (Year: 2014).*
Broad et al. J. Extracell. Vesicles, 2023, 12, e12309, pp. 1-6 (Year: 2023).*

Li et al. BIOI 2021, 2, 29-36 (Year: 2021).*
Lin et al. Adv. Sci. 2018, 5, 1700611 (Year: 2018).*
Sukhmandeep et al. Cancer Letters 2023, 566, 216243 (Year: 2023).*
Patel et al. International Journal of Pharmaceutics 2021, 607, 120943 (Year: 2021).*
Brenneman, D.E. et al. Knockdown siRNA Targeting the Mitochondrial Sodium-Calcium Exchanger-1 Inhibits the Protective Effects of Two Cannabinoids Against Acute Paclitaxel Toxicity. J Mol Neurosci. Aug. 2019; 68(4): 606-619.
King, K.M. et al. Single and combined effects of Delta9-tetrahydrocannabinol and cannabidiol in a mouse model of chemotherapy-induced neuropathic pain. British Journal of Pharmacology (2017) 174, 2832-2841.
Britch, S.C. et al. Cannabidiol: Pharmacology and Therapeutic Targets. Psychopharmacology (Berl). Jan. 2021; 238(1): 9-28.
Mlost, J. et al. Cannabidiol for Pain Treatment: Focus on Pharmacology and Mechanism of Action. Int. J. Mol. Sci. 2020, 21, 8870.
Ward, S.J. et al. Cannabidiol inhibits paclitaxel-induced neuropathic pain through 5-HT 1A receptors without diminishing nervous system function or chemotherapy efficacy. British Journal of Pharmacology (2014) 171, 636-645.
Lee, M.J. Effect of subcutaneous treatment with human umbilical cord blood-derived multipotent stem cells on peripheral neuropathic pain in rats. Korean J Physiol Pharmacol 2017;21(2):153-160.
Gallily, R. et al. Cannabidiol (CBD) Prevents Palmitic Acid-Induced Drop in Mitochondrial Membrane Potential. Pharmacology & Pharmacy, 2019, 10, 387-395.
Kang, S. et al. Cannabidiol Induces Autophagy to Protects Neural Cells From Mitochondrial Dysfunction by Upregulating SIRT1 to Inhibits NF-κB and NOTCH Pathways. Frontiers in Cellular Neuroscience, Mar. 2021, vol. 15, Article 654340.
Atalay, S. et al. Antioxidative and Anti-Inflammatory Properties of Cannabidiol, Antioxidants 2020, 9, 21.
Jesus, C.H.A, et al. Cannabidioil attenuates mechanical alloydynia in streptozotocin-induced diabetic rats via serotonergic system activation through 5-HT1A receptors. Brain Research 1715 (2019) 156-164.
Bisogno, T. et al. Molecular targets for cannabidiol and its synthetic analogues: effect on vanilloid VR1 receptors and on the cellular uptake and enzymatic hydrolysis of anandamide. British Journal of Pharmacology (2001) 134, 845-852.
Blessing, E.M. Cannabidiol as a Potential Treatment for Anxiety Disorders. Neurotherapeutics (2015) 12:825-836.
Pascual, D. et al. A cannabinoid agonist, WIN 55,212-2, reduces neuropathic nociception induced by paclitaxel in rats. Pain 118 (2005) 23-34.
Sagredo, O. et al. Cannabidiol reduced the striatal atrophy caused 3-nitropropionic acid in vivo by mechanisms independent of the activation of cannabinoid, vanilloid TRPV1, and adenosine A2A receptors. European Journal of Neuroscience, vol. 26, pp. 843-851.

(Continued)

*Primary Examiner* — Matthew P Coughlin

(74) *Attorney, Agent, or Firm* — Anton J. Hopen; Trenam Law

(57) ABSTRACT

A composition and method of treating diabetes or chemotherapy-induced neuropathy is presented. The composition is comprised of at least one extracellular vesicle encapsulating at least one cannabinoid. Administration of a therapeutically effective amount of this composition of extracellular vesicles encapsulating at least one cannabinoid can be used to treat both diabetic and chemotherapy-induced neuropathic pain in a patient.

9 Claims, 24 Drawing Sheets

(56)          References Cited

OTHER PUBLICATIONS

Ward. S.J. Cannabidiol Prevents the Development of Cold and Mechanical Allodynia in Paclitaxel-Treated Female C57BI6 Mice. Anesth Analg. Oct. 2011; 113(4): 947-950.

Gangadaran, P. et al. Extracellular vesicles from mesenchymal stem cells activates VEGF receptors and acclerates recovery of hindlimb ischemia. Journal of Controlled Release 264 (2017) 112-126.

Do Monte, F.H. et al. Infusion of cannabidiol into infralimbic cortex facilitates fear extinction via CB1 receptors. Behavioural Brain Research 250 (2013) 23-14.

Shiue, S.J. et al. Mesenchymal stem cell exosomes as a cell-free therapy for nerve injury-induced pain in rats. Pain, Jan. 2019. vol. 160, 210-223.

Patel, N. et al. Cannabidiol loaded extracellular vesicles sensitize triple-negative breast cancer to doxorrubicin in both in-vitro and in vivo models. Internation Journal of Pharmaceutics, 607 (2021) 120943.

De Medieros Ramalho, I.M. et al. Current trends on cannabidiol delivery systems: where are we and where we are going? Expert Opinion on Drug Delivery, DOI: 10.1080/17425247.2021.1952978.

Perucca, Emilio and M. Bialer. Critical Aspects Affecting Cannabidiol Oral Bioavailablity and Metabolic Elimination, and Related Clinical Implications. CNS Drugs, Jun. 5, 2020. https://doi.org/10.1007/s40263-020-00741-5.

Kola, B. et al. Cannabinoids increase AMP-activated protein kinase (AMPK) enzyme activity in the hypothalamus and heart via different signaling pathways—studies in CB1 knockout animals. Endocrine Abstracts (2006) 11 OC25 . . . .

Kalvala, A. K. et al. Role of Cannabidiol and Tetrahydrocannabivarin on Paclitaxel-induced neuropathic pain in rodents. Int Immunopharmacol. Jun. 2022 ; 107: 108693. doi: 10.1016/j.intimp.2022.108693.

* cited by examiner

Figure 1A-I

***P<0.001 vs   Control, ^^^p<0.001 , ^^p<0.01 & ^p<0.05    vs PTX (8 mg/kg)

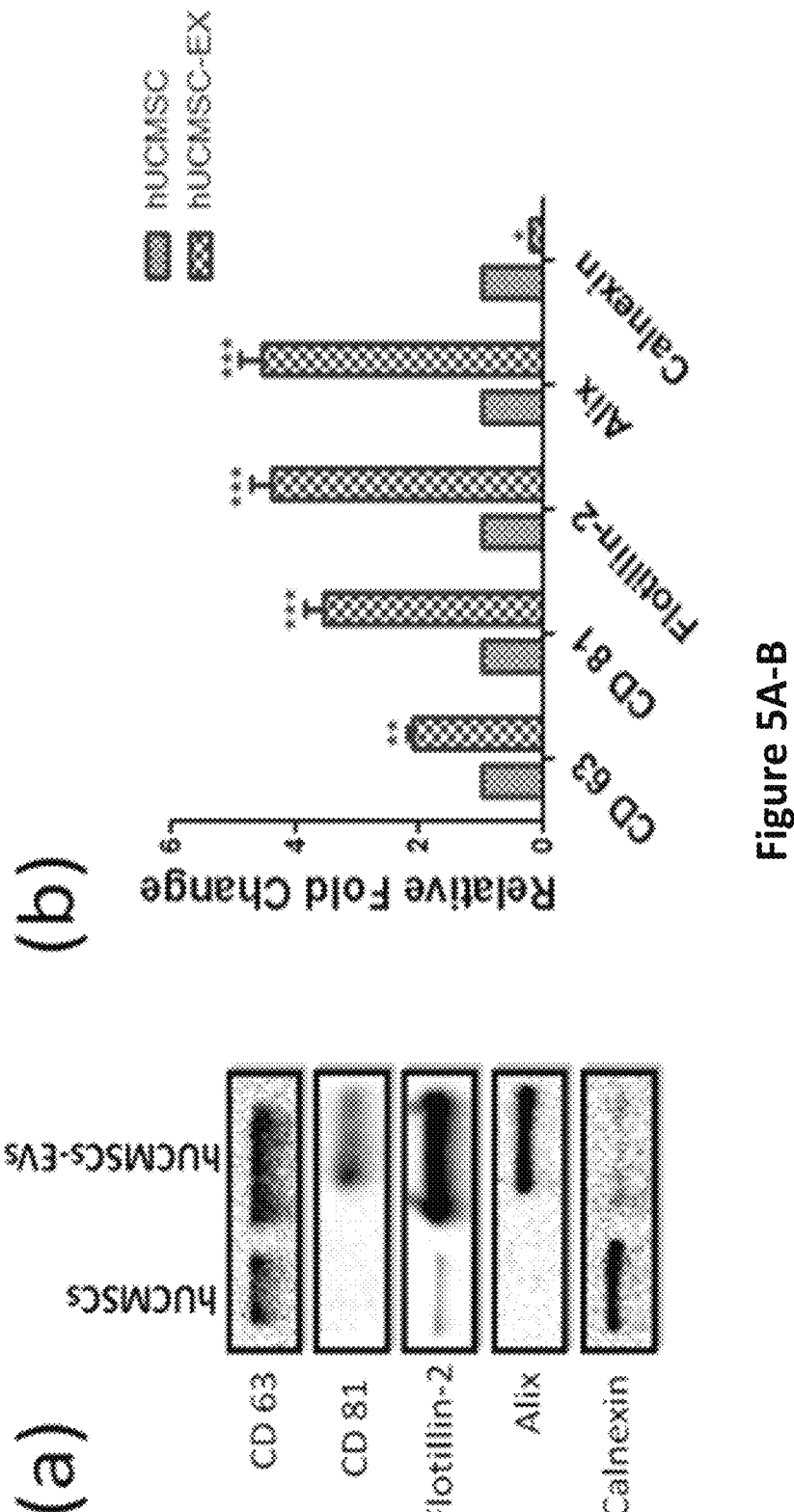
Figure 5A-B (c)

(d)

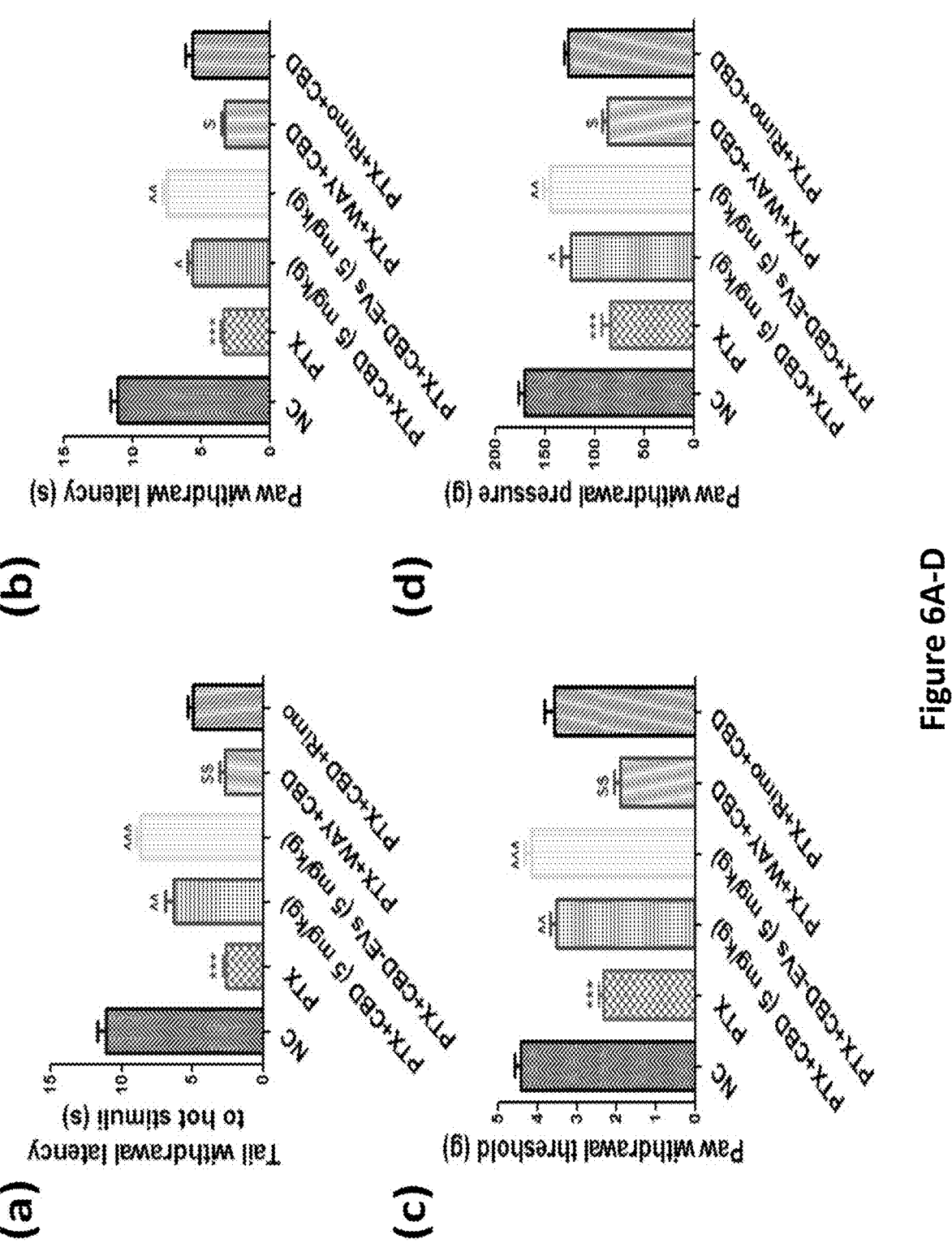
Figure 6A-D

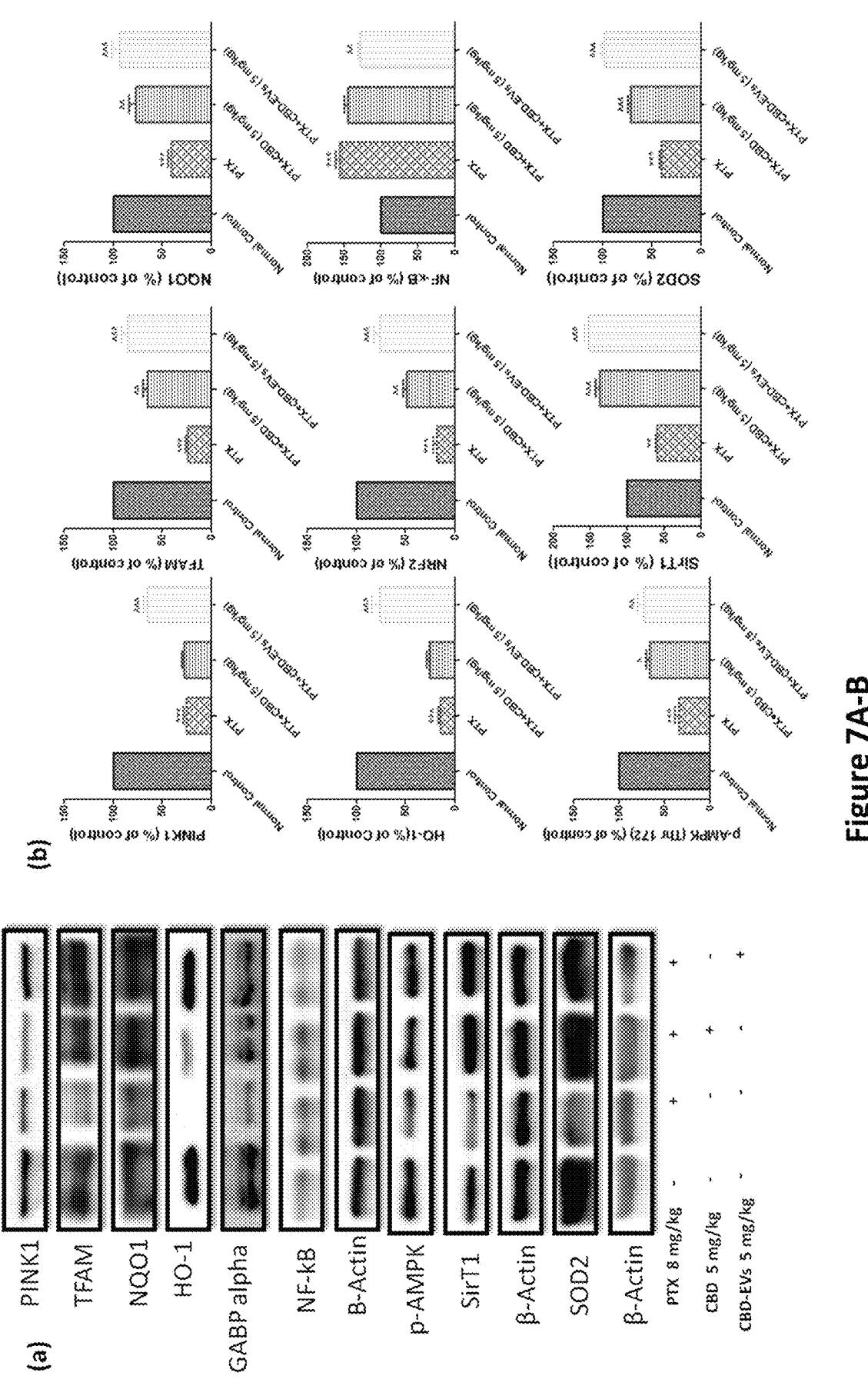
Figure 7A-B

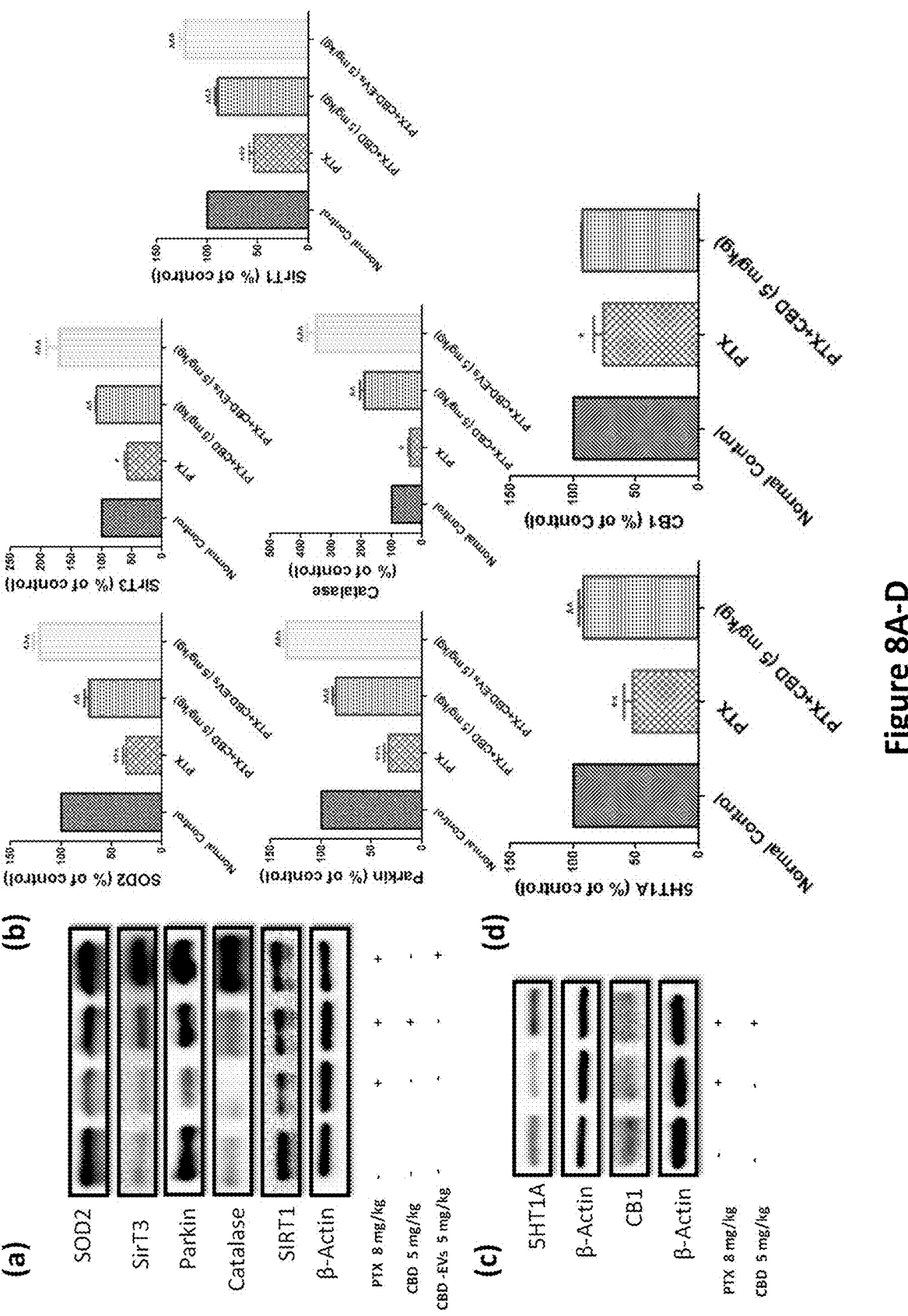
Figure 8A-D

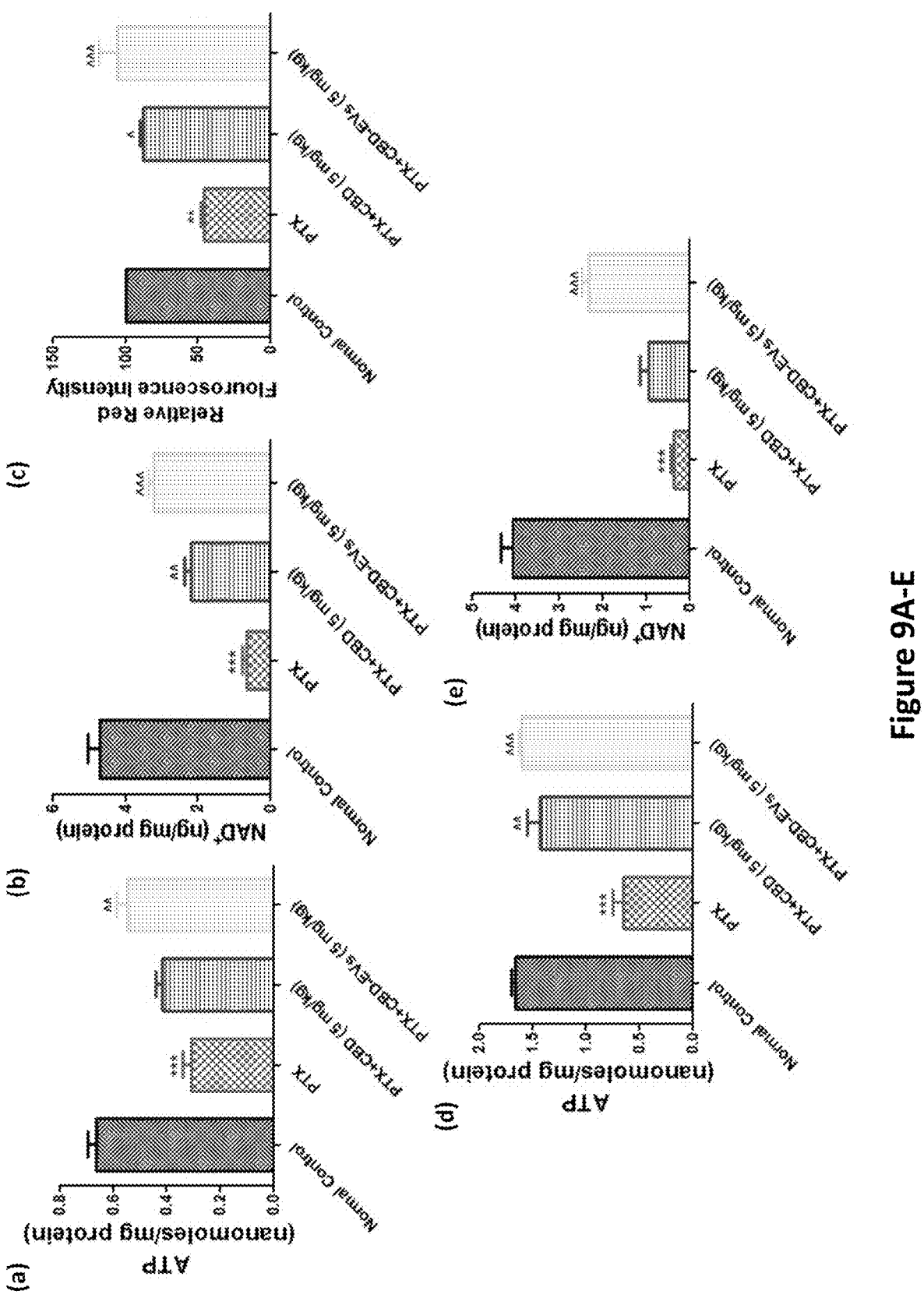
Figure 9A-E

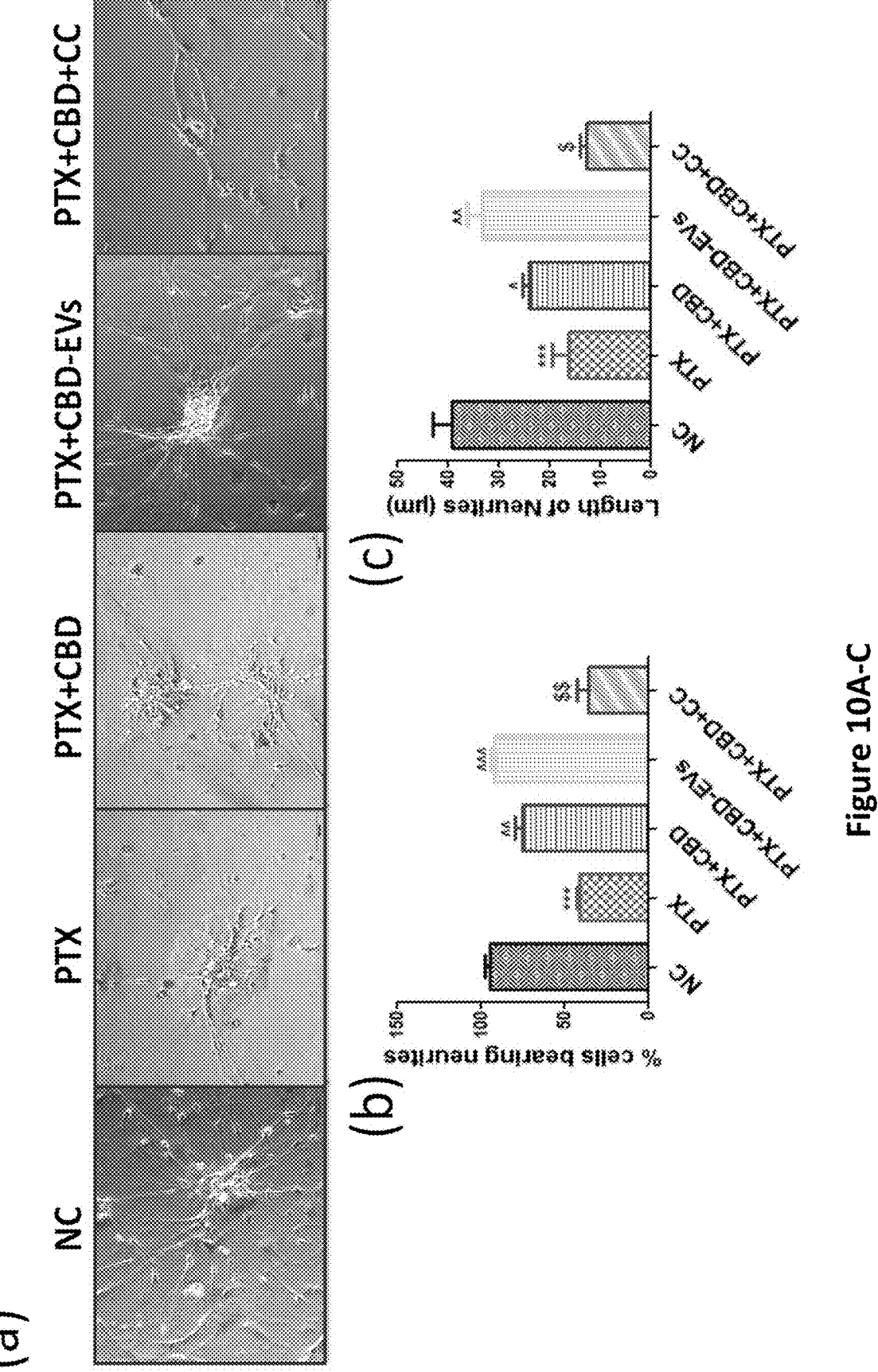
Figure 10A-C

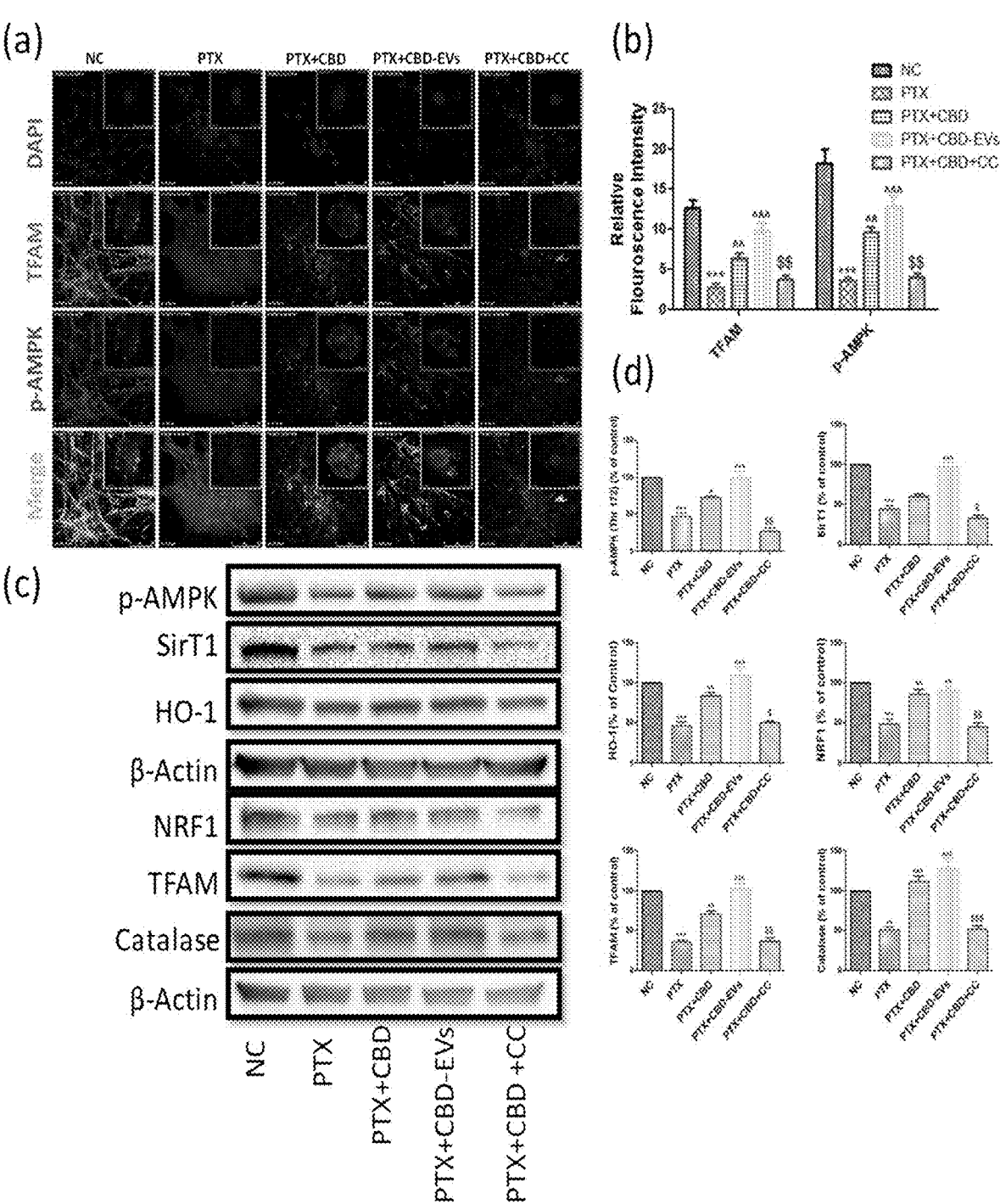
Figure 11A-D

FIG. 16C

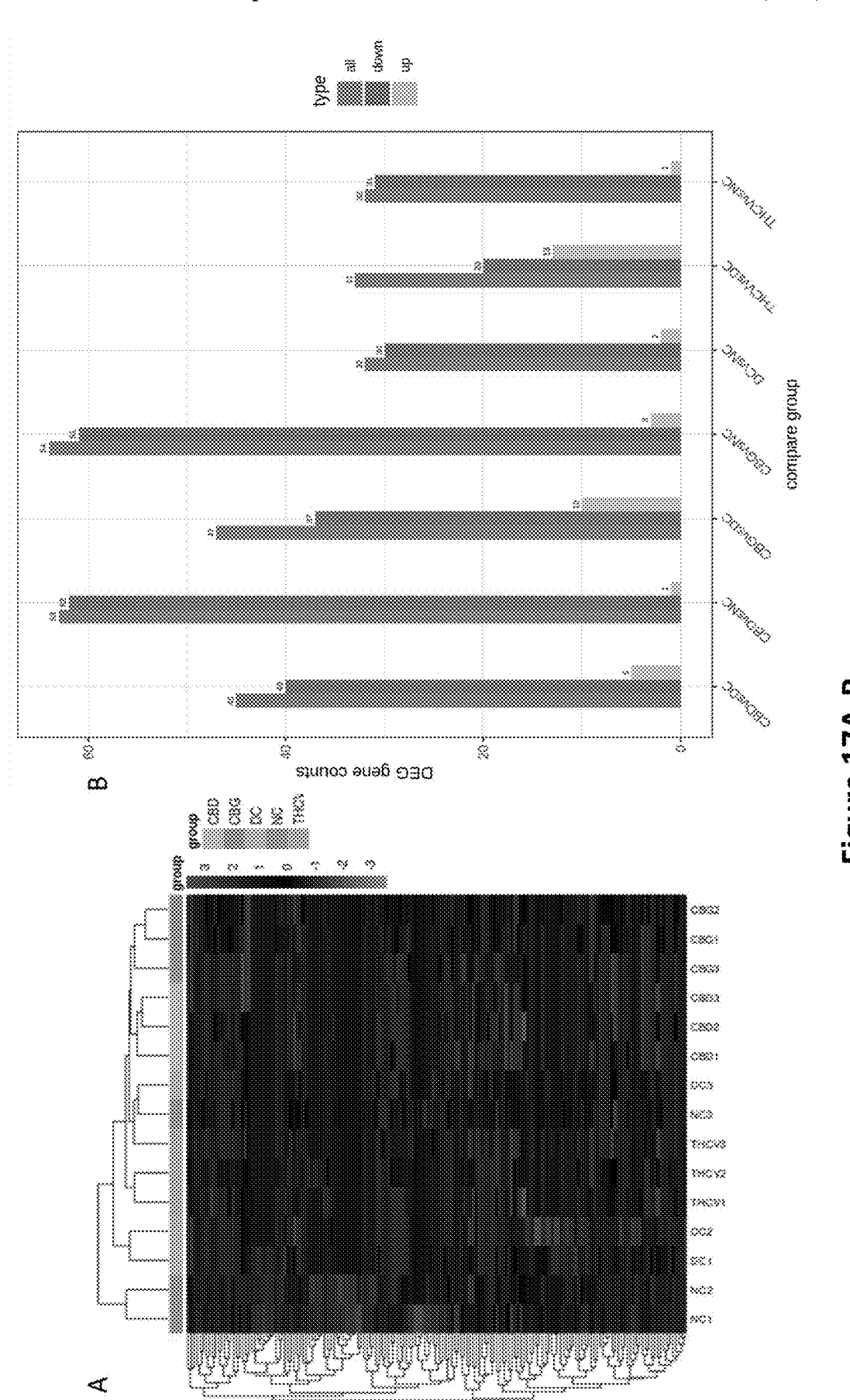
Figure 17A-B

CANNABINOID COMPOSITION AND METHOD OF TREATING DIABETIC AND CHEMOTHERAPY INDUCED NEUROPATHIC PAIN

CROSS REFERENCE TO RELATED APPLICATIONS

This application is a nonprovisional of and claims priority to U.S. Provisional Patent Application Ser. No. 63/212,238, entitled "Cannabinoid Composition and Method of Treating Diabetic and Chemotherapy Induced Neuropathic Pain", filed Jun. 18, 2021, the contents of which are hereby incorporated by reference into this disclosure.

GOVERNMENT SUPPORT

This invention was made with Government support under Grant No. U54 MD007582 awarded by the National Institute on Minority Health and Health Disparities of the National Institutes of Health (NIH) and Grant No. 1735968 awarded by the National Science Foundation (NSF)-CREST Center for Complex Materials Design for Multidimensional Additive Processing (CoManD). The Government has certain rights in the invention.

FIELD OF INVENTION

This invention relates to compounds and methods of treatment for neuropathic pain. Specifically, the invention provides cannabinoid compounds and methods of treatment using such for neuropathic pain caused by diabetes or chemotherapy.

BACKGROUND OF THE INVENTION

Diabetic Neuropathy

Diabetes is the leading cause of neuropathy in USA and around 60-70% of the people with diabetes often experience neuropathy. Painful burning sensations, tingling, numbness in hands and feet, foot ulcers and limb amputations are very common in patients suffering from diabetic peripheral neuropathy (DPN). Treatment options for DPN are very limited and often ineffective. Some DPN patients take antidepressants for symptomatic relief but are experiencing CNS side effects. Glycemic control can delay the progression of neuropathy but it does not show much in reducing DPN. Multiple factors are involved, including poor understanding of pathophysiology and ineffective drugs, which challenge the identification of novel targets and new drugs to treat DPN.

Chemotherapy Induced Neuropathy

Another type of neuropathic pain is from chemotherapy. For example, the taxane class (paclitaxel and docetaxel) are widely used for the treatment of triple-negative breast cancer but peripheral neuropathy (PN) is one of the major dose-limiting and serious unwanted side effects of these drugs. Neuropathic pain is due to the pain resulting from damage to the somatosensory nervous system. It is generally characterized by abnormal sensations (dysesthesia), exaggerated pain perception to a nociceptive stimuli (hyperalgesia) or pain arising from non-painful stimuli (allodynia). Neuropathic pain is common in cancer and can be either as a direct result of cancer on peripheral nerves (e.g., compression by a tumor), or due to the side effects of chemotherapy. The prevalence of chemotherapy induced peripheral neuropathy (CIPN) is around 11-87% with clinical usage of taxanes and are higher with platinum-based drugs.

Paclitaxel (PTX) is the most potent drug in the taxanes group and is used to treat aggressive and metastatic breast, ovarian, pancreatic, non-small-cell lung and Kaposi's sarcoma cancers[1]. It has been reported that weekly PTX treatment offers better progression free survival than nab-PTX and ixabepilone in patients with advanced breast cancer[2]. However, the incidence of neuropathy from PTX is one of the major clinical challenges which has a very high prevalence ranging from 11 to 87%[3]. It can lead to development of sensory dominant neuropathy manifesting clinical outcomes like paraesthesias, dysesthesia, altered proprioception, numbness, and loss of sensitivity in the fingers and finger tips 4. These symptoms are dose dependent can continue up to 1-3 years after cessation of the therapy and can sometimes last lifelong. However, current therapies for PTX induced neuropathic pain are only partially effective and the underpinning mechanisms for developing PTX induced neuropathic pain are not fully understood. Therefore, there is an imperative need to develop a therapy which does not impede anti-tumor efficacy but effectively controls PTX induced neuropathic pain (PIPN).

Mitochondrial dysfunction associated with dysregulation of AMPK-SIRT1 (Sirtuin 1)-NRF1/2 (nuclear respiratory factor 1/2)-TFAM (Mitochondrial transcription factor A) axis has been implicated in several neuronal diseases which include Alzheimer's disease, parkinsonism, diabetic neuropathy, nerve injury, Huntington's disease, and PIPN[5-7]. Cannabidiol (CBD), a major non-psychoactive component of *Cannabis sativa*, has an important role in regulating the pain associated with different conditions[8, 9] and also has been shown to be effective in managing breast cancer, psoriasis, human epithelial carcinoma, colon cancer, inflammatory bowel disease, glaucoma, platelet aggregation and also acts as antidote for psychoactive cannabinoids [10]. However, CBD has poor solubility and is susceptible to degradation via the action of light and temperature in solution form and undergoes extensive first pass metabolism [11]. Thus, a properly formulated version of CBD can play a crucial role in enhancing its physiochemical stability and therapeutic efficacy. Of note, inhalational formulations of these compounds produced irritation to the lungs, transdermal patches irritated mucosa and nano formulations in different polymers showed entrapment and drug release problems [12].

Recently, the inventors have established isolation and characterization procedures for extracellular vesicles (EVs) derived from mesenchymal stem cells/stromal cells (hUCMSCs). These EVs proved to be efficient in reducing neuropathic pain by their paracrine secretions. hUCMSCs-derived EVs shuttle bioactive components such as proteins, lipids, mRNA, miRNA, lncRNA, circRNA, and DNA that participate in Schwann cell regeneration, macrophage activation, and reconstruction of vascular networks to repair the nerve damage[13]. Accumulating literature also suggests that EVs derived from hUCMSCs could activate AMPK pathway to alleviate viral myocarditis and cannabinoids could activate hypothalamic AMPK to stimulate appetite in mouse models[14]. AMPK activation offers neuroprotection by manipulating oxidative stress, inflammation, autophagic deficits, endoplasmic reticulum stress and mitochondrial dysfunction[15].

Cannabidiol (CBD) has shown to activate multiple receptors in different disease models[16]. Ward et al., demonstrated that the activation of 5HT1A receptors by CBD was responsible for improving neuro behavioral characteristics of mice against PIPN[17]. Further, Polter et al., showed that 5HT1A blocker (8-OH-DPAT) treatment reduced calcium/calmodulin dependent protein kinase II (CaMKII) phosphorylation[18]. CaMKII has the ability to activate AMPK by phosphorylation and known to involve in regulating mitochondrial homeostasis[19, 20].

Presently, no study has been conducted to understand the role of CBD loaded in hUCMSCs-derived EVs in PIPN. The inventors have evaluated the effect of CBD and CBD-EVs formulation on oxidative stress and mitochondrial function via targeting endocannabinoid and non-endocannabinoid receptors and AMPK pathway. To accomplish these objectives, the inventors have isolated and characterized the EVs from hUCMSCs. Further, the inventors investigated the pharmacological effects of CBD and CBD-EVs administration on pathophysiological indices of neuropathy in PTX treated mice and cultured primary dorsal root ganglion (DRG) neurons (isolated from rat spinal region (L1-L5). 5HT1A and CB1 blockers and Compound C (AMPK inhibitor) were used to validate the pharmacological mechanism of CBD in offering neuroprotection. The results offer significant leads and insights in the role of CBD and CBD-EVs in treatment of chemotherapy induced peripheral neuropathy.

In light of the limited treatment options for neuropathic pain such as DPN and CIPN including PIPN, what is needed is a novel neuropathy treatment capable of overcoming the shortcomings of the prior art.

SUMMARY OF INVENTION

Minor phytocannabinoids, CBD, CBG and THCV have gained much attention as therapeutic agents in various applications (e.g. anxiety, ageing, cancer, pain etc.) and their effect on DPN is one unexplored area. In preclinical studies, CBG displayed protective effects against LPS induced neuroinflammation by alleviating oxidative stress, inflammation, and autophagy defects. THCV reduced obesity and diabetes in rodent studies by acting as a direct antioxidant through functioning as a neutral antagonist for CB1 receptors and partial agonist for CB2 receptors. As CBD, CBG, and THCV have shown earlier promise in attenuating chronic diabetic pain in small patient studies, it is expected that a combination treatment of CBD or CBG and THCV would have an entourage effect in attenuating DPN.

In some embodiments, administering a therapeutically effective amount of a combination of THCV and CBD or CBG and THCV is used for treating diabetic neuropathic pain. In order to deliver these cannabinoids more effectively, a combination of THCV and CBG or CBD and THCV was used in exosomes. The exosomes were used in SHYS5Y cell lines with high glucose induced. CBD exosomes, CBD and THCV were also studied in a paclitaxel induced neuropathic pain model and behavioral parameters were monitored.

In some embodiments relating to chemotherapy-induced neuropathic pain, CBD was formulated in extracellular vesicles (CBD-EVs) isolated from human umbilical cord derived mesenchymal stem cells and was characterized for its particle size, stability and release studies. Further, the effect of CBD-EVs was evaluated for the first time against paclitaxel (PTX) induced neuropathic pain (PIPN) in C57BL/6J mice. PTX (8 mg/kg, i.p.) was injected every other day (four doses) to induce neuropathy (evident by increased mechanical and thermal hyperalgesia/allodynia, $p<0.01$). CBD and CBD-EVs treatment displayed significant improvement in mechanical and thermal hypersensitivity ($p<0.001$). Molecular investigations in DRG and spinal homogenates of PTX treated mice demonstrated mitochondrial dysfunction via deregulated AMPK-SIRT1-NRF2 axis and CBD-EVs treatment significantly ($p<0.01$) corrected mitochondrial function by regulating this pathway. CBD treatment had no effect on neurobehavior and mitochondrial function against PIPN after blocking 5HT1A receptors with WAY100135 and AMPK with compound C respectively. The data suggests that CBD-EVs reduced PIPN by manipulating AMPK pathway and mitochondrial function.

In an embodiment, a method of treating neuropathy in a patient in need thereof is presented comprising administering, to the patient in need thereof, a therapeutically effective amount of a composition comprising at least one cannabinoid encapsulated within at least one extracellular vesicle and a pharmaceutically acceptable carrier wherein the administration of the composition treats the neuropathy of the patient.

The neuropathy may be induced by diabetes or chemotherapy. The at least one cannabinoid may be selected from the group consisting of Cannabidiol (CBD), Cannabigerol (CBG), Tetrahydrocannabivarin (THCV), and combinations thereof. In some embodiments, the at least one cannabinoid is CBD. In another embodiment, the at least one cannabinoid is THCV. In other embodiments, the at least one cannabinoid is a combination of CBD and THCV or a combination of CBG and THCV.

The at least one extracellular vesicle can be derived from at least one umbilical cord stem cell, such as a human umbilical cord mesenchymal stem cell. The extracellular vesicle may be an exosome.

In another embodiment, a composition for treating neuropathy in a patient in need thereof is presented comprising at least one extracellular vesicle encapsulating at least one cannabinoid and a pharmaceutically acceptable carrier.

The at least one cannabinoid can be encapsulated in the at least one extracellular vesicle via sonication or sonoporation. The at least one extracellular vesicle may be derived from at least one umbilical cord mesenchymal stem cell. The at least one extracellular vesicle may be an exosome.

The at least one cannabinoid may be selected from the group consisting of Cannabidiol (CBD), Cannabigerol (CBG), Tetrahydrocannabivarin (THCV), and combinations thereof. In some embodiments, the at least one cannabinoid is CBD. In another embodiment, the at least one cannabinoid is THCV. In other embodiments, the at least one cannabinoid is a combination of CBD and THCV or a combination of CBG and THCV.

In a further embodiment, a method of treating diabetic peripheral neuropathy in a patient in need thereof is presented comprising administering a therapeutically effective amount of at least one cannabinoid to the patient in need thereof wherein after administration the diabetic peripheral neuropathy is treated.

In some embodiments, the at least one cannabinoid is encapsulated in at least one extracellular vesicle. The at least one extracellular vesicle may be derived from at least one umbilical cord mesenchymal stem cell. The at least one extracellular vesicle may be an exosome.

Whether encapsulated or administered alone, the at least one cannabinoid may be selected from the group consisting of Cannabidiol (CBD), Cannabigerol (CBG), Tetrahydrocannabivarin (THCV), and combinations thereof. In some embodiments, the at least one cannabinoid is CBD. In another embodiment, the at least one cannabinoid is THCV. In other embodiments, the at least one cannabinoid is a combination of CBD and THCV or a combination of CBG and THCV.

BRIEF DESCRIPTION OF THE DRAWINGS

For a fuller understanding of the invention, reference should be made to the following detailed description, taken in connection with the accompanying drawings, in which:

FIG. 5A-D are a series of images depicting isolation and characterization of CBD loaded EVs (hUCMSCs): (A) western blots and (B) densitometric analysis of exosomal markers CD 63, CD 81, Flotillin-2, and stem cell marker Calnexin in human umbilical cord derived stem cells (hUCMSCs) lysates and extra cellular vesicles protein lysates derived from hUCMSC (hUCMSCs-EVs). (C) Histogram represents the mean particle size distribution of CBD-EVs and (D) representative line plot showing % cumulative release of CBD from extracellular vesicles in PBS at PH 7.4 and 6.8 respectively at different time points.

FIG. 6A-D are a series of images depicting the effect of CBD and CBD-EVS on neurobehavior of PTX induced neuropathic mice. Bar graphs represent (A) Hot immersion test (B) Hargreaves plantar test, (C) Vonfrey test, and (D) Randall Selitto test, Values are expressed as mean±SEM (n=3). ***p<0.001 Vs NC, ^p<0.05, ^^p<0.01 and ^^^p<0.001 Vs PTX (8 mg/kg), $P<0.05 and $$P<0.01 Vs PTX+CBD (5 mg/kg).

FIG. 7A-B are a series of images depicting the effect of CBD and CBD-EVs on AMPK-SIRT1-NRF1/2 Axis. (A) Western blots of DRG homogenates from PTX treated mice show treatment with CBD (5 mg/kg) and CBD-Exo (5 mg/kg) for six weeks after last dose of PTX administration.

(B) Bar graphs represent the respective western blots quantification. Values are expressed as mean±SEM (n=3). ***p<0.001 Vs Normal control, ^p<0.05, ^^p<0.01 and ^^^p<0.001 Vs PTX (8 mg/kg).

FIG. 8A-D are a series of images depicting the effect of CBD and CBDEVs on AMPK-SIRT1-NRF1/2 Axis in spinal homogenates and effect of CBD on CB1 and 5HT1A receptors expression in DRG homogenates of PTX induced neuropathic mice. (A) Western blots of spinal homogenates show treatment with CBD (5 mg/kg) and CBD-EVs (5 mg/kg) and (C) Western blots of DRG homogenates show treatment with CBD (5 mg/kg) in PTX treated mice for six weeks after last dose of PTX administration. (B) & (D) Bar graphs represent the respective western blots quantification. Values are expressed as mean±SEM (n=3). ***p<0.001 Vs Normal control, ^p<0.05, ^^p<0.01 and ^^^p<0.001 Vs PTX (8 mg/kg).

FIG. 9A-E are a series of images depicting the effect of CBD and CBD-EVs on Mitochondrial Function and mitochondrial membrane potential (ΔΨm). (A) Representative bar graphs showing the ATP levels in Fresh DRG homogenates and (D) spinal homogenates of PTX treated mice, (B) bar graph showing NAD+ levels in DRG homogenates and (E) in spinal homogenates of PTX treated mice, (C) Bar graph represents the JC1 trimer aggregates relative red florescence intensity. Values are expressed as mean±SEM (n=3). ***p<0.001 Vs Normal control, ^p<0.05, ^^p<0.01 and ^^^p<0.001 Vs PTX (8 mg/kg).

FIG. 10A-C are a series of images depicting the effect of CBD and CBD-EVs on neuritogenesis in cultured DRG cells isolated from L1 to L5 spinal region of Rats. (A) Representative photomicrographs captured by using phase contrast microscope (40×) showing the neurite extensions coming out from each DRG cell, (B) bar graphs represents the percent of cells bearing neurites and (C) bar graph represent the image j analysis of neurite length of untreated and treated groups. ***p<0.001 Vs NC, ^p<0.05, ^^p<0.01 and ^^^p<0.001 Vs PTX (8 mg/kg), $P<0.05 and $$P<0.01 Vs PTX+CBD.

FIG. 11A-D are a series of images depicting immunoexpressions of AMPK pathway in cultured DRG primary cells (A) Representative confocal microscope images showing the upper panel nuclear (DAPI) staining, middle panel: immunoexpression of TFAM tagged with Alexa488 fluorochrome and lower panel: immunoexpression of p-AMPK labeled with rhodamine, (B) quantified relative red and green florescence intensities of confocal images using LASX software associated with confocal microscopy. (C) Western blots of cultured DRG lysates show treatment with 12 μM either of CBD and CBD-EVs in PTX treated neuronal cells for 48 hours (D) Bar graphs represent the respective western blots quantification. ***p<0.001 Vs NC, ^p<0.05, ^^p<0.01 and ^^^p<0.001 Vs PTX (8 mg/kg). $P<0.05, $$P<0.01 and $$$P<0.001 Vs PTX+CBD.

Figure 12:
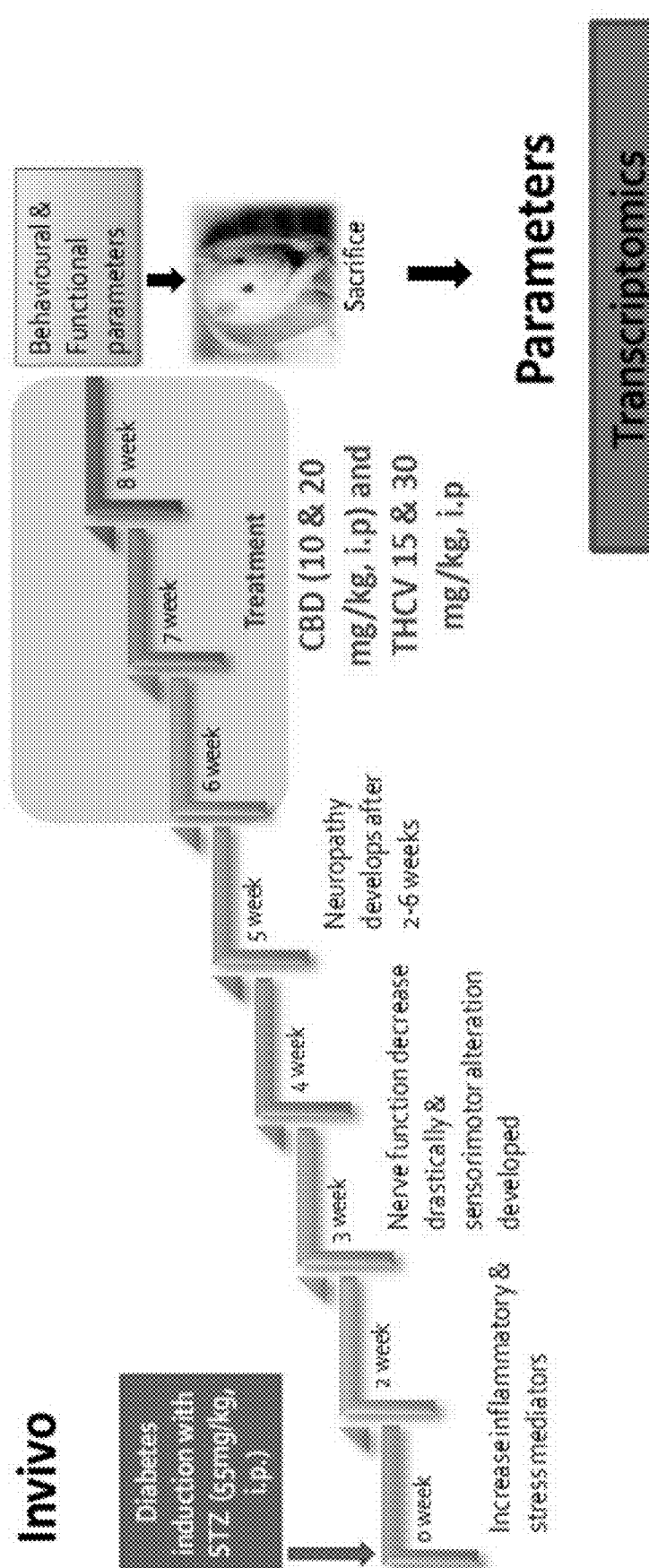

FIG. 12 is an image depicting the experimental plan for identifying the transcriptomic signatures of Cannabidiol (CBD) and tetrahydrocannabivarin (THCV) in Streptozotocin induced experimental diabetic neuropathy (DN).

Figure 13:
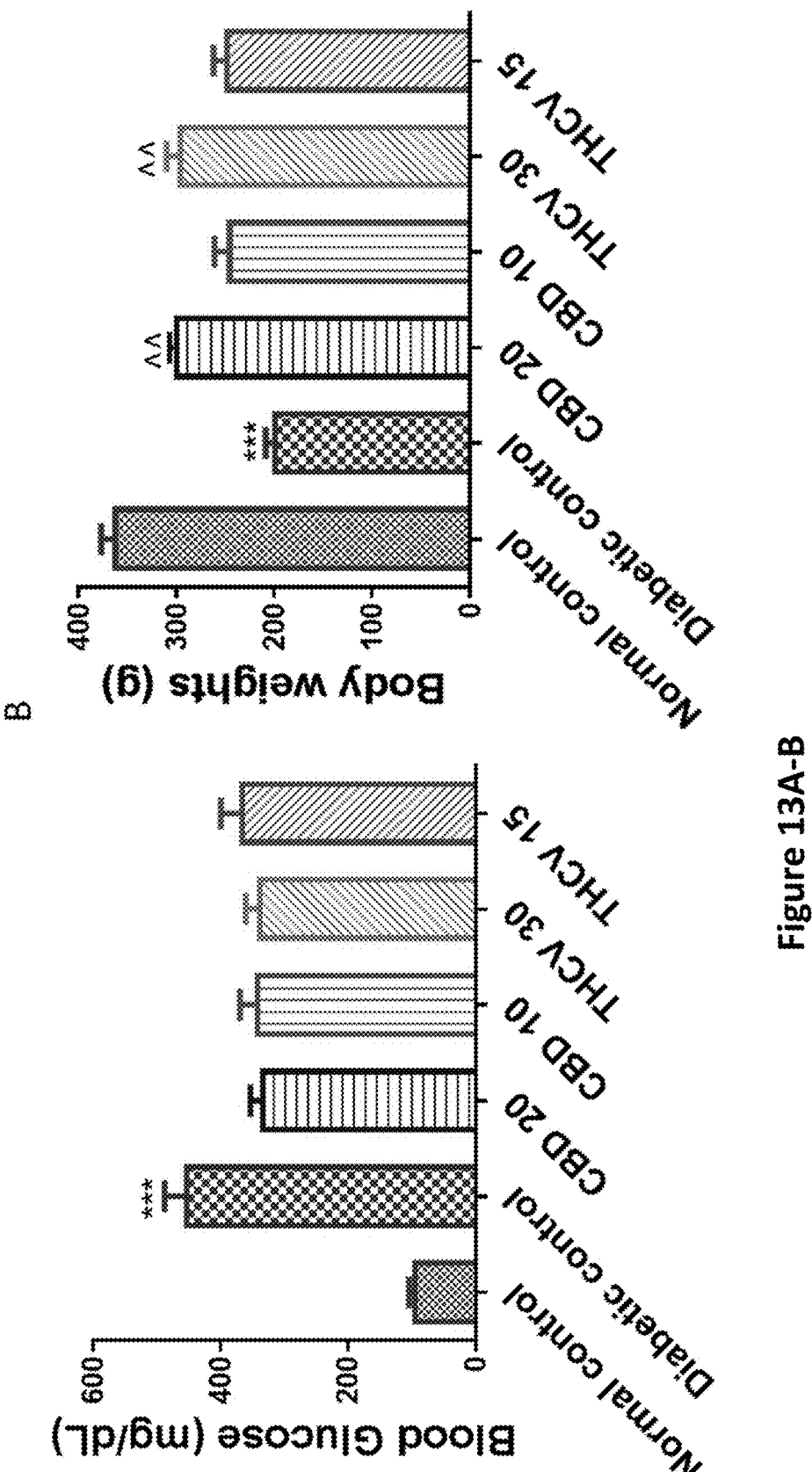
Figure 14:
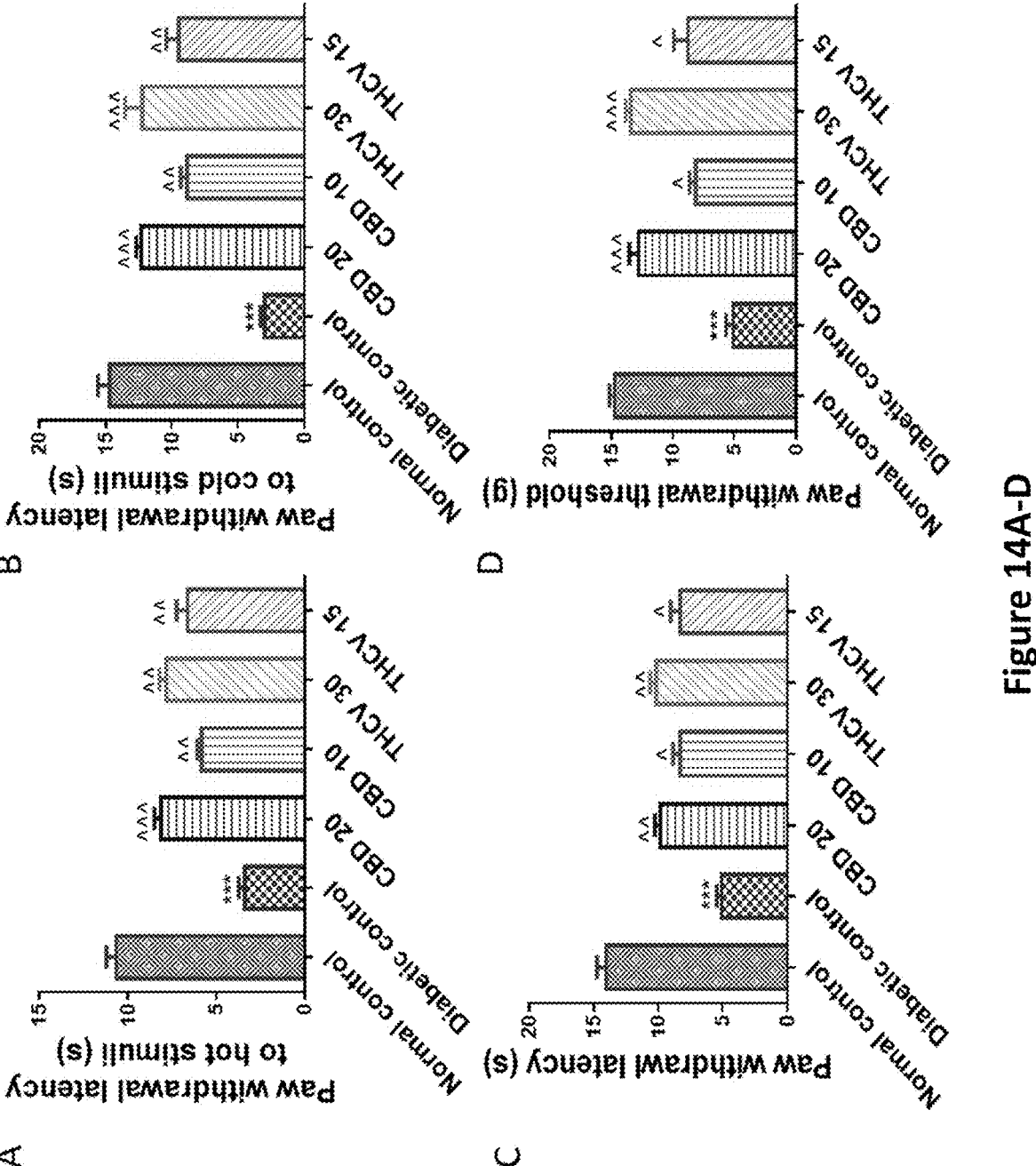

FIG. 13A-B are a series of graphs depicting the effects of minor phytocannabinoids (CBD and THCV) on animal body weights and blood glucoses levels. Results are expressed as mean±SEM (n=6). ***P<0.001 vs. normal control & ^^p<0.01 vs. diabetic control.

FIG. 14A-D are a series of graphs depicting the effects of minor phytocannabinoids (CBD & THCV) on thermal pain in diabetic animals. Representative histograms of paw withdrawal latencies to (A) hot stimuli, (B) cold stimuli and (C)

infrared heat applied by hot plate, cold plate and Hargreaves apparatus respectively and (D) paw withdrawal threshold in grams (Von Frey) after the last day dose to diabetic animals of eight weeks study. Results are expressed as mean±SEM (n=6). ***$P<0.001$ Vs Normal control & ^$p<0.05$, ^^$p<0.01$ & ^^^$p<0.001$ Vs Diabetic control.

Figure 15:
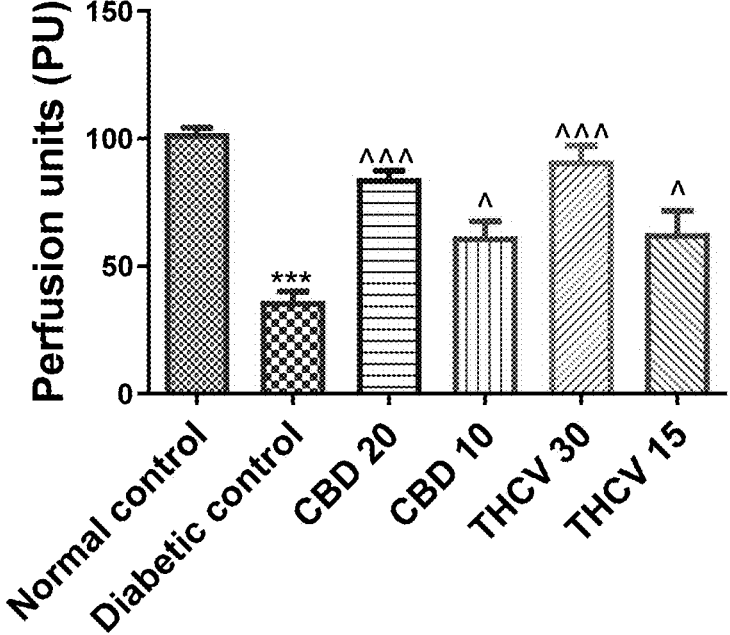

FIG. 15 is a graph depicting the effects of minor phyto-cannabinoids (CBD and THCV) on sciatic nerve blood flow in diabetic animals. Representative histograms showing nerve blood flow measured in perfusion units after the last day dose to diabetic animals of eight weeks study. Results are expressed as mean±SEM (n=6). ***$P<0.001$ Vs Normal control & ^$p<0.05$, ^^$p<0.01$ & ^^^$p<0.001$ Vs Diabetic control.

Figure 16A:
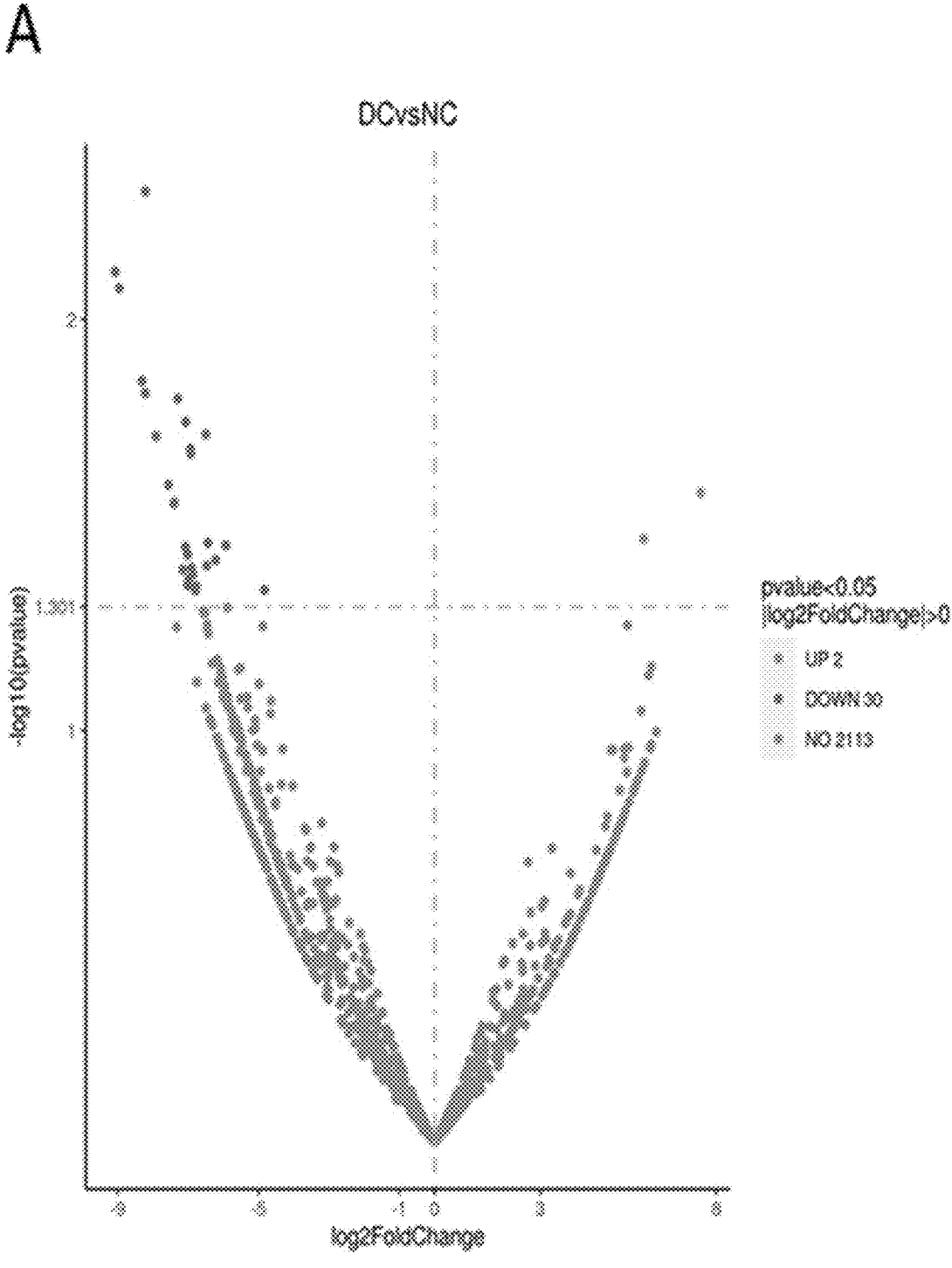
Figure 16B:
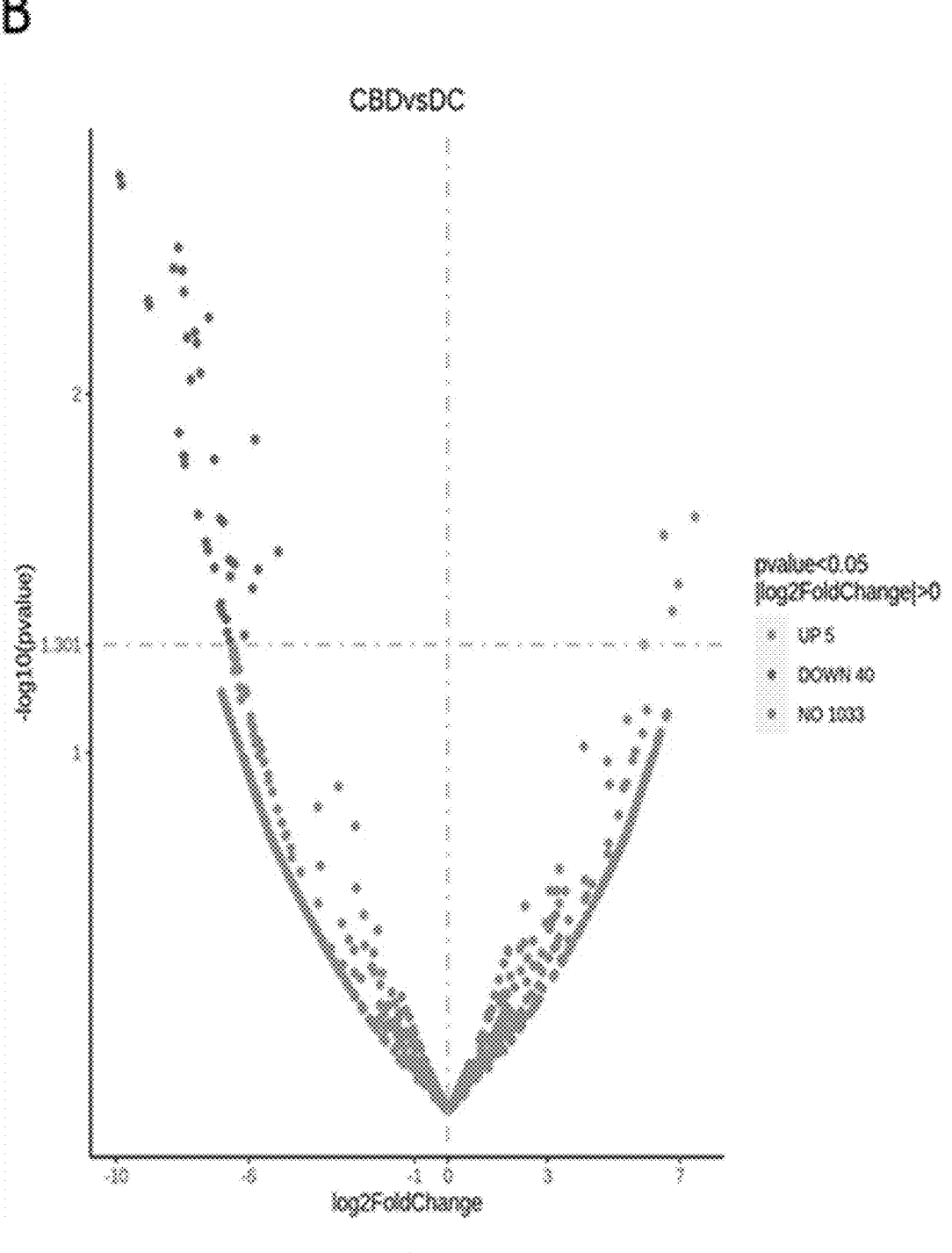

FIG. 16A-C are a series of images depicting differentially expressed genes (DEGs) from RNA-Seq data. Volcano plots of significant differentially expressed genes of (A) Cannabidiol (CBD) vs. diabetic control (DC), (B) Tetrahydrocannbivarin (THCV) vs. DC and (C) Non diabetic (NC) vs. DC groups. CBD: 10 weeks of diabetic rats received CBD (10 mg/kg/day, i.p) for last four weeks, THCV: 10 weeks of diabetic rats received THCV (15 mg/kg/day, i.p) for last four weeks, and CBG: 10 weeks of diabetic rats received CBG (15 mg/kg/day, i.p) for last four weeks. Data was expressed as Mean±SEM (n=3). Gene Ontology (GO) of differentially expressed genes was implemented by the clusterProfiler R package, in which gene length bias was corrected. GO terms with corrected P value less than 0.05 were considered significantly enriched by differential expressed genes.

FIG. 17A-B are a series of images depicting Differentially expressed genes (DEGs) in DRG homogenates of diabetic rats from RNA-Seq data. (A) Heatmap hierarchical clustering revealed the DEGs related to the treatment of Cannabidiol (CBD), tertrahydrocannabivarin (THCV) and Cannabigerol (CBG) to STZ induced diabetic neuropathy rats (DC) and (B) bar graph represents the total, down regulated and upregulated DEGs in different combinations of treated, untreated and disease group animals. Data was expressed as Mean±SEM (n=3).

Figure 18:
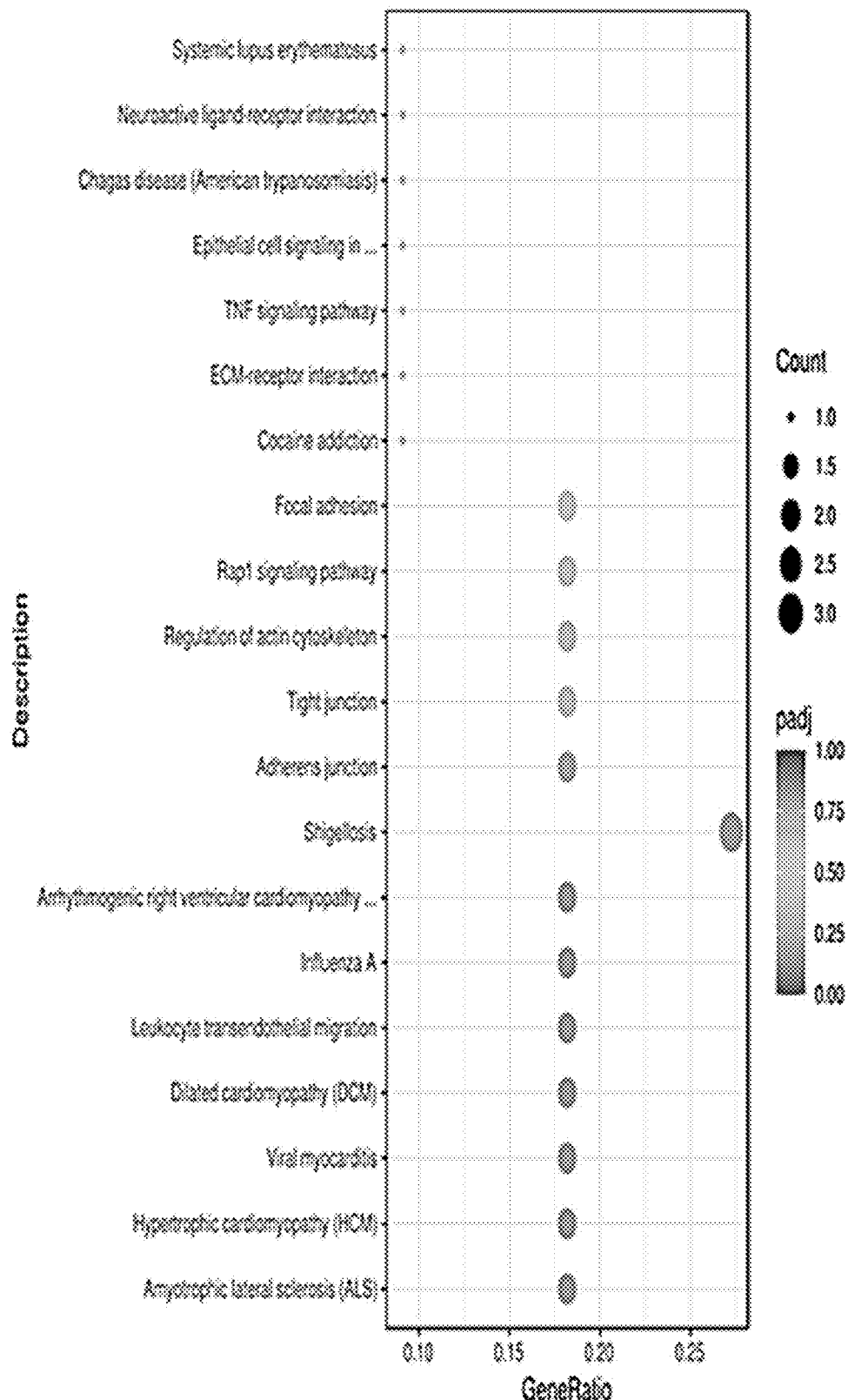
Figure 18:
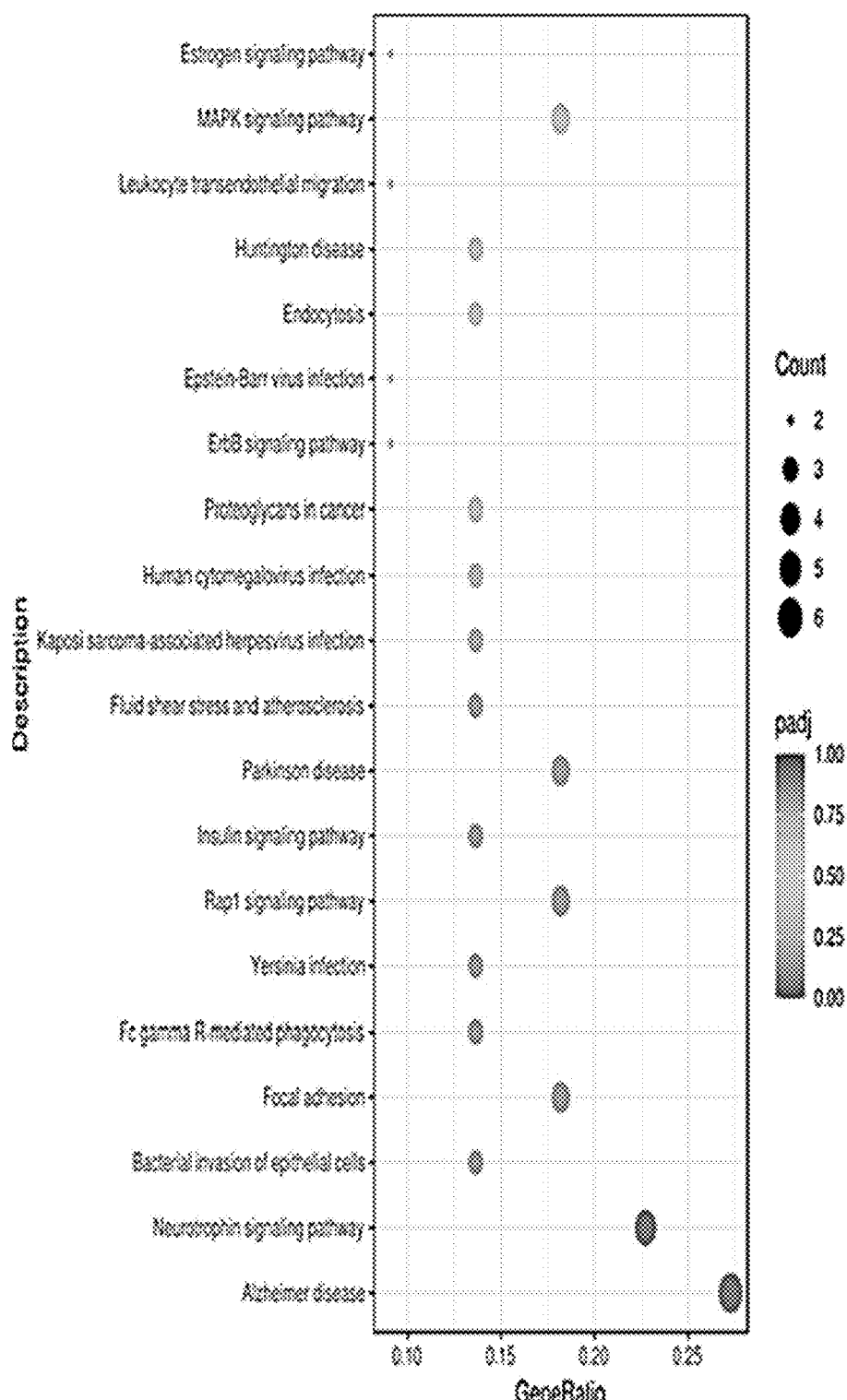
Figure 18:
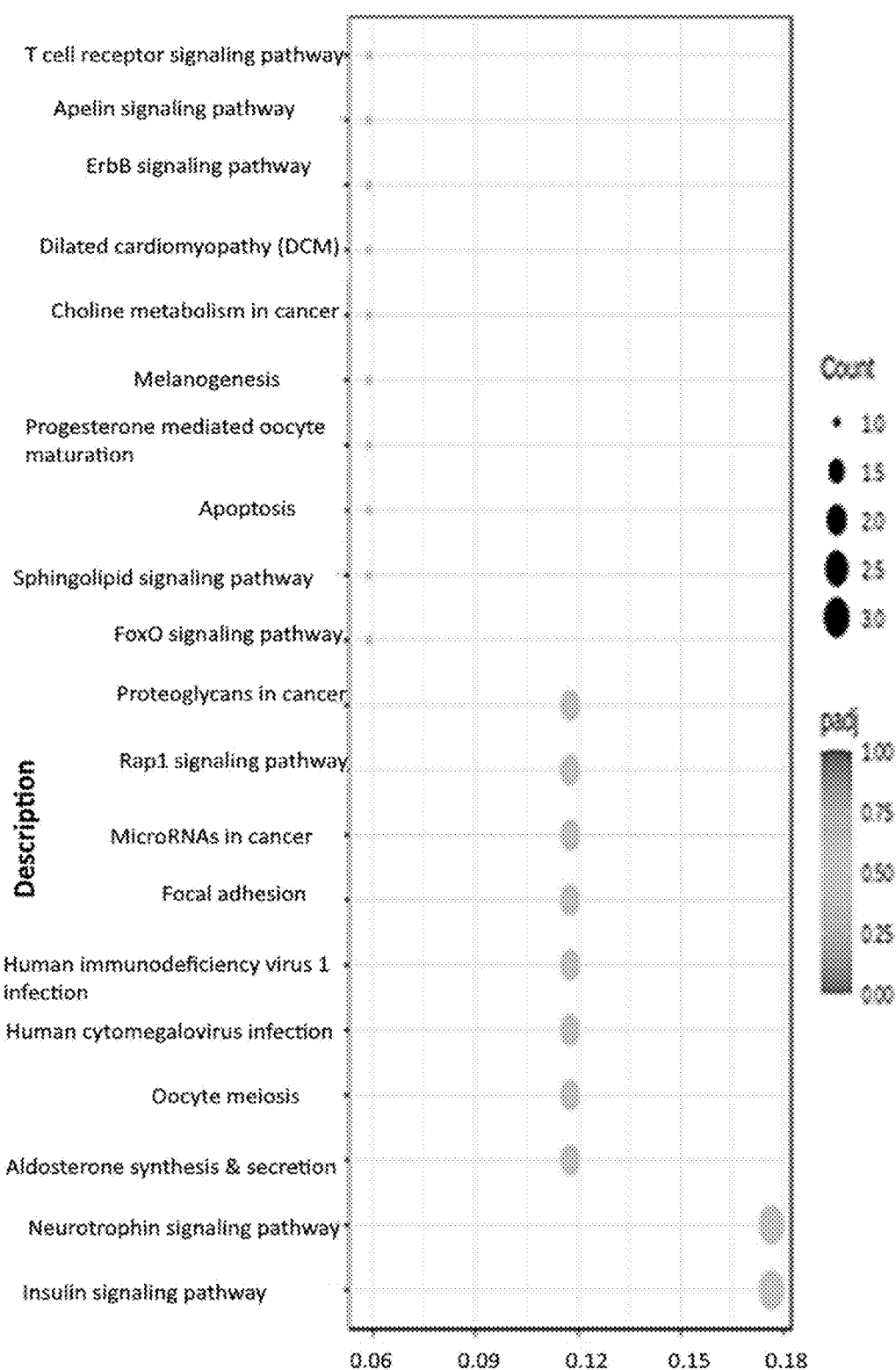

FIG. 18 is a series of images depicting differentially expressed genes (DEGs) from RNA-Seq data by KEGG pathway Analysis. Bubble plots comparing the top 20 significant DEGs pathways in DRGs of diabetic and control group rats, DRGs of CBD and THCV treated diabetic rats vs. diabetic group animals. Data was expressed as Mean±SEM (n=3). KEGG enrichment analysis of differentially expressed genes was implemented by the clusterProfiler R package, in which gene length bias was corrected. KEGG terms with corrected P value less than 0.05 were considered significantly enriched by differential expressed genes.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Abbreviations

CBD—Cannabidiol
CBG—Cannabigerol

CIPN—Chemotherapy Induced Peripheral Neuropathy
DPN—Diabetic Peripheral Neuropathy
DRG—Dorsal Root Ganglion
EVs—Extracellular Vesicles
hUCMSCs—Human Umbilical Cord Mesenchymal Stem Cells
PTX—Paclitaxel
PIPN—Paclitaxel Induced Neuropathic Pain
TFAM—Transcription Factor A, Mitochondrial
THC—Tetrahydrocannabinol
THCV—Tetrahydrocannabivarin

Definitions

As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, "about" means approximately or nearly and in the context of a numerical value or range set forth means±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein "patient" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include humans, rodents, mammals, aquatic mammals, domestic animals such as dogs and cats, and farm animals such as sheep, pigs, cows and horses. Wherein the terms "animal" or the plural "animals" are used, it is contemplated that it also applies to any animals.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W Easton Pennsylvania, Mack Publishing Company, 19th ed.) describes formulations which can be used in connection with the subject invention.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; releasing agents; sterilizing agents; sweeteners; solubilizers; wetting agents; and mixtures thereof.

As used herein, "administering" or "administration" refers to the process by which the compounds of the present invention are delivered to a subject. The compounds of the present invention may be administered in a variety of ways including, but not limited to, buccally, orally, nasally, or parenterally (intramuscularly, intraperitoneally, intrasternally, intravenously, subcutaneously). Any of the compounds may also be delivered through encapsulation in vesicles such as extracellular vesicles such as exosomes and microvesicles, liposomes, niosomes, micelles, etc.

"Extracellular vesicles" as used herein refers to nanometer-sized lipid bound vesicles secreted into the extracellular space. Extracellular vesicles (EVs) include, but are not limited to, exosomes (intraluminal vesicles) and microvesicles. In some embodiments, the EVs are derived from umbilical cord stem cells such as human umbilical cord mesenchymal stem cells.

The term "compound" as used herein refers to a chemical formulation, either organic or inorganic, that induces a desired pharmacological and/or physiological effect on a subject when administered in a therapeutically effective amount. "Compound" is used interchangeably herein with "drug" and "therapeutic agent".

"Treatment" or "treating" as used herein refers to any of: the alleviation, amelioration, elimination and/or stabilization of a symptom or characteristic, as well as delay in progression of a symptom of a particular disorder. For example, "treatment" of cancer may include any one or more of the following: amelioration and/or elimination of one or more symptoms/characteristics associated with neuropathic pain, reduction of one or more symptoms/characteristics of neuropathic pain, stabilization of symptoms/characteristics of neuropathic pain, and delay in progression of one or more symptoms/characteristics of neuropathic pain.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with cancers. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

Example 1—Preliminary Studies

Effect of CBD, CBG and THCV on mitochondrial function in high glucose exposed SH-SY5Y cells:

Briefly, SH-SY5Y cells were obtained from ATCC and were cultured in EMEM: F12 medium in 1:1 ratio (containing 5.5 mM glucose) supplemented with 10% FBS, glutamine (2 mM), streptomycin/penicillin (1%) and grown at 37° C. in a humidified atmosphere of 95% air and 5% CO2. High glucose (HG) condition was simulated by addition of 24.5 mM glucose to make the final concentration of glucose in the medium to 30 mM. This concentration of glucose is well demonstrated to simulate in vivo diabetic peripheral neuropathy condition. The cells were then processed for MTT studies and MitoSox staining.

MTT Studies:

MTT studies were performed using SH-SY5Y cells and the $IC_{25}$ concentrations of CBD, THCV, and CBG were ascertained to assess their neuroprotective potential. The results showed that CBD, THCV, and CBG showed significant neurotoxicity at concentrations greater than 12.5 $\mu M$ ($IC_{50}$: 11.6 $\mu M$), 25 $\mu M$ ($IC_{50}$: 16.9 $\mu M$) and 25 $\mu M$ ($IC_{50}$: 15.74 $\mu M$) respectively.

MitoSox Staining:

MitoSox-based flow cytometry was performed to evaluate mitochondrial superoxides in SH-SY5Y cells according to the previously published procedures with slight modifications. Briefly, after 3h of treatment with the cannabinoids, cells were incubated with 5 $\mu M$ of Mitosox red for 10 min and PBS washing was performed. After trypsinization and centrifugation, the pellets were resuspended in FBS containing PBS and subjected to fluorescence analysis using BD FACSVerse (BD Biosciences, CA, USA). CBD (6 $\mu M$) and CBG (8.5 $\mu M$) in huMSC derived exosomes formulation treatment significantly reduced mitochondrial superoxides (P<0.001) in SH-SY5Y cells when compared to HG treated cells.

Methodology for Mouse Studies

C57 mice were injected with Paclitaxel (PTX) i.p. with a dose of 8 mg/kg every other day for 4 days. After confirming with various behavioral parameters that neuropathy has been induced, various treatments were given with 5 mg/kg CBD, THCV, and CBD exosomes via i.p. route. Various behavioral parameters were then noted for up to 48 days and responses were plotted.

Methodology for Preparation and Administration of Exosomes

Exosomes were prepared from umbilical cord MSCs and by using a series of centrifugation steps were then characterized for their protein markers. The exosomes containing CBD were formulated by using an established procedure in the laboratory.

Results

The results showed that CBD, CBG, and THCV had beneficial effects in reducing superoxides in high glucose SHY5SY cells. Further, the results conducted with C57 mice which had Paclitaxel induced neuropathy demonstrated that THCV, CBD, and CBD exosomes could make significant changes in their behavioral function as assessed by Von Frey and Randal Sellito apparatus. A 7-week experiment demonstrated significant improvement in paw withdrawal latency and threshold responses. These results strongly suggest the role of cannabinoids like THCV, CBD, CBG and their combinations in neuropathy which could be induced by diabetes or chemotherapy through multiple mechanisms.

Conclusion

Presently there is not a good treatment for diabetic or chemotherapy induced neuropathy. Using uHMSCs derived exosomes, neural stem cell derived exosomes or ipsc derived exosomes containing CBD and THCV combination or CBG and THCV combination is able to give good relief for diabetic neuropathic pain. The formulation is made with exosomes containing CBD and then a lipid bilayer containing either THCV or CBG is then incorporated on top of the exosome layer by using sonication or sonoporation.

Example 2—Treatment of Chemotherapy Induced Neuropathic Pain

Paclitaxel (PTX) is a widely used anticancer drug for the treatment of many common cancers including lung, breast, prostate and gynecologic malignancies. However, neuropathy is an irreversible side effect of PTX limiting its clinical usage in the cancer chemotherapy.

hUCMSCs have an ability to promote neurite outgrowth and can repair damaged peripheral neurons by secreting various neurotropic factors e.g. nerve growth factor, fibroblast growth factor, hepatocyte growth factor, brain derived neurotropic factor, and insulin-like growth factor[25]. Exosomes isolated from Schwann cells have shown improved dorsal root ganglion (DRG) cell proliferation and inhibition of apoptosis and cell senescence in injured DRG cells[26]. However, no study has been reported on the role of exosomes/EVs derived from hUCMSCs in regulation of neuropathic pain. The inventors are the first to demonstrate the neuroprotective effects of extracellular vesicles (EVs) encapsulating CBD against PIPN.

The use of CBD as a therapeutic agent is hindered by its poor stability and lack of stability due to oxidation. To overcome this limitation, the inventors developed a CBD-EVs formulation. The significance of CBD loaded EVs in the treatment of triple negative breast cancers in athmyic nude mice was recently reported[21]. The CBD-EVs were formulated and the release studies showed that more than 60 percent of CBD was released by 24 h at pH 6.8 and 7.4. Moreover, exosomes express definite endosomal pathway markers including tetraspanins (CD63 and CD81), heat shock proteins (HSP70) and Rab family proteins such as TSG101 and Alix [27]. Consistent with earlier reports, the inventors also observed the expression of tetraspanins, alix and flotillin 2 in exosomal lysates derived from hUCMSCs. Calnexin was considered as a negative protein marker of exosomes[28] which is also underexpressed in hUCMSCs-EVs lysates.

Here, mechanical and thermal pain sensitivity increased in PTX treated mice and the reversal of this pain by CBD administration was consistent with the published reports [17]. The statistical significance in reversing the PTX induced pain in mice with CBD administration was two-fold less when compared with CBD-EVs formulation suggesting an additive, if not synergistic effect of the CBD-EV formulation described herein. Lee et al. showed that EVs (derived from hUCMSCs) administration recuperated nerve ligation-induced mechanical and thermal hypersensitivities of rats[29]. Additionally, hUCMSCs decreased the pain hypersensitivity associated with chronic constriction injury, spinal nerve ligation and spared nerve injury in rats[30]. These findings suggest that addition of EVs with CBD may have additive/synergistic effects in attenuating PTX induced neuropathic pain.

PIPN is associated with the development of spontaneous activity and hyper excitability in DRG neurons which contributes for tremendous pain[31]. The inventors also observed molecular changes in isolated DRGs from PTX treated mice and PTX treated cultured DRGs isolated from rats. PTX is known to reduce mitochondrial function thereby precipitating sensory neuropathies. PTX treatment halted the growth of neurites in cultured DRGs which has also been suggested in earlier reports[32]. Interestingly, CBD and CBD-EVs increased neurite outgrowths in DRGs and length of neurites against PTX insult in cultured DRG cells. Further, compound C treatment prior to CBD treatment showed no improvement of PTX induced neurite outgrowths reduction in cultured DRGs. This data suggests that CBD-EVs have superior effects in improving neural circuits against PTX induced disturbances. However, CBD may enhance this neurite outgrowth through activation of AMPK as evident by showing its neutral effects in presence of compound C, which is a well-known AMPK inhibitor and has been articulated in several reports[33].

The inventors found that PTX administration significantly decreased the ATP and NAD+ levels in both DRG and spinal homogenates of mice which directly correlates to unhealthy mitochondria. CBD markedly improved mitochondrial biogenesis and mitochondrial function against doxorubicin induced cardiotoxicity[34]. Likewise herein, CBD treatment partially enhanced ATP and NAD+ levels in both DRG and spinal homogenates of PTX treated mice. However, the CBD-EVs formulation improved ATP and NAD+ levels in a superior fashion than CBD alone in both DRG and spinal homogenates of mice. To support this data, a study conducted by Zhou et al., showed that EVs derived from hUCMSCs expressed PINK1 protein and treatment with them improved mitochondrial homeostasis against sepsis-induced mitochondrial dysfunction in cardiomyocytes[35]. Moreover, the inventors observed reduction of PINK1 protein expression in DRG homogenates of PTX treated mice and significantly increased expression of PINK1 after treatment with CBD and CBD-EVs. The enhanced improvement of ATP and NAD+ levels with CBD-EVs may be attributable to the expression of PINK1 in EVs derived from hUCMSCs.

Moreover, EVs derived from hUCMSCs improved mitochondrial function by increasing mitochondrial membrane potentials as evidenced by JC1 staining in human pulmonary microvascular endothelial cells against LPS induced cellular damage[36]. CBD also enhanced mitochondrial repolarization in macrophages and microglia cells against saturated palmitic acid exposure[37].

The inventors also observed CBD and CBD-EVs treatment prevented PTX induced drop in mitochondrial membrane potential in dissociated DRG cells of mice. The improvement of mitochondrial membrane potentials with CBD-EVs formulation was two-fold higher than CBD alone treatment. Given the results, the inventors propose the CBD-EVs formulation has a synergistic effect in enhancing mitochondrial membrane potentials.

AMPK is considered a metabolic manipulator as well as an energy sensing kinase and has emerged as a novel pharmacological target for the treatment of chronic pain due to its ability in regulating oxidative stress, inflammation, mitochondrial function, biogenesis, autophagy and endoplasmic reticulum stress[15]. The inventors demonstrated that PTX treatment downregulated the expression of p-AMPK in both DRG's of in vitro and in vivo studies suggesting its role in PIPN. Similarly, studies conducted by Inyang et al., also reported that administration of AMPK activators alleviated PTX induced mechanical hypersensitivity and hyperalgesic effects in male and female mice[38]. Indeed, cannabinoids can improve AMPK activity by different signaling mechanism in improving appetite and cardiac function[39]. Additionally, it has been reported that EVs (derived from hUCMSCs) also enhanced AMPK activity in rescuing myocardial ischemia[14]. These reports suggest that CBD and EVs combination can improve AMPK since CBD-EVs formulation increased the expression of p-AMPK in DRG homogenates of PTX treated mice and DRG neuronal cells. The inventors have also analyzed downstream signaling of AMPK pathway to understand the effects of CBD-EVs against PIPN in mice.

DRG and spinal homogenates of PTX treated mice displayed significant reduction of SirT1 expression which is in line with a study by Xiaoning et al., who have shown that resveratrol treatment reduced thermal and mechanical pain associated with PTX administration in rats by increasing SirT1 expression[40]. AMPK activation raises the intracellular NAD+ levels and activates SIRT1 which results in deacetylation and translocation of nuclear factors NRF1 and NRF2 into the nucleus. CBD and CBD-EVs also enhanced NAD+ levels and SirT1 protein expression in DRG and spinal homogenates of PTX treated mice. These findings suggest that AMPK regulated by CBD-EVs could enhance NAD+ levels and thereby SirT1 expression. CBD has previously shown to enhance autophagy and mitochondrial function in human neuroblastoma cells (Parkinsonism in vitro model) by activating SirT1 pathway. It has also been reported that knockdown of SirT1 by siRNA transfection pauses the autophagy and mitochondrial functional effects of CBD against MPP+-induced SHSY5Y cells[41]. However, the inventors inhibited AMPK activity by compound C (dorsomorphin) treatment and have observed failure of CBD to enhance SirT1 protein in PTX insulted DRG primary cells. The inventors believe this is the first study showing CBD dependent effects on AMPK in maintaining mitochondrial health of neuronal cells. However, in agreement with previous reports the inventors also observed down regulation of NRF1 and NRF2 (GABPa) expressions in DRG homogenates of PTX treated mice. NRF1 and NRF2 are the transcription factors which play a crucial role in regulating transcription of important mitochondrial proteins. Enhanced phosphorylation of AMPK activates a myriad of downstream proteins and NRF1/2 are the key proteins affected to regulate mitochondrial biogenesis and mitochondrial function. It has been reported that transcriptional activity of NRF1/2 regulates the TEAM expression in the neuronal cells[42]. PTX treatment significantly reduced the expressions of NRF1/2 in DRG homogenates of mice and treatment with CBD reversed this effect and in presence of compound C, CBD failed to increase the expression of NRF1/2. The down regulation of NRF1/2 proteins in peripheral neurons of PTX treated mice and its upregulation (dependent on AMPK activity with CBD and CBD-EVs treatment) were found for the first time here.

Transcription factor A, mitochondrial (TFAM) has an extensive role in regulation of mitochondrial genome and embryonic development in mammalian cells[43]. PTX treatment has shown to decrease maximal respiration, spare respiratory capacities, ATP production and mitochondrial membrane depolarization in isolated DRG neurons[44] which was also observed by the inventors. However, in the present study, CBD-EVs treatment showed more a potent significant ($p < 0.001$) effect in reversing mitochondrial membrane depolarization and ATP production in DRG neurons of PTX treated mice. These results illustrate CBD in EVs formulations have superior mitoprotective effects than CBD alone. It is important to find out the isolated EVs cargo in detail including proteins, lipids, nucleic acids and other cellular components to understand the mitoprotective role of CBD in EVs formulation. CBD has demonstrated a significant role in mitigating oxidative stress as a direct antioxidant[45]. However, in the present study, the inventors observed increased expressions of SOD2, NQO1 and HO1 with CBD and its EVs formulations against PIPN in mice. In addition to regulating mitochondrial bioenergetics, AMPK also activates Nrf2 and NF-κB signaling pathways which mainly regulates oxidative stress and inflammation[46]. Moreover, phosphorylation of AMPK at Thr 172 site by therapeutic interventions maintained redox imbalance and inflammatory pool by balancing the Nrf2 and NF-κB pathways[47]. In line with these findings, CBD and CBD-EVs treatment to PTX treated mice increased the expression of antioxidant enzymes and decreased phosphorylation of NF-κB in DRG and spinal tissue homogenates.

In the present study, PTX administration to mice reduced the expressions of 5HT1A and CB1 receptors in DRG homogenates of neuropathic mice and CBD treatment significantly improved the 5HT1A receptors expression without any effect on CB1 expression. These findings are supported by a recent study by Sara et al., who reported that that CBD offers neuroprotection by selectively activating 5HT1A receptors[17]. Further, 5HT1A receptor agonist treatment protected the retina from oxidative damage and mitochondrial dysfunction[48]. In another study, CBD showed protection against STZ induced diabetic pain by selectively activating 5HT1A receptors[49]. Pascual et al. demonstrated that administration of CB1/CB2 dual agonist WIN55,212-2 suppressed the thermal hyperalgesia and tactile allodynia induced by PTX in rats and this effect was blocked by the CB1 antagonist SR141716, suggesting the involvement of the CB1 receptor[50].

In another study, intraventricular infusion of CBD into infralimbic cortex of rat brain reduced the anxiety parameter (extinction test) which was hypothesized to be stimulated by activating CB1 receptors[51]. However, Segrado et al., and Sara et al., have shown neither CB1 nor CB2 receptors involvement of CBD's ability in reducing neuropathic pain[17,52]. Moreover, very limited studies have demonstrated that CBD has less binding affinity for CB1 or CB2 receptors despite its indirect activation of CB1/CB2 receptors by enhancing endocannabinoid levels[53,54]. In agreement with previous reports, the inventors found that CBD anti-nociceptive effects are not dependent upon CB1 activation (FIG. 8). Moreover, it has been demonstrated that 5HT1A receptors plays a vital role in phosphorylation of CaMKII which is a upstream regulator of AMPK pathway[19]. Thus, the results may explain the potential of CBD activating 5HT1A receptors and AMPK pathway in regulating mitochondrial bioenergetics, redox and inflammatory balance of neuronal cells and activation by CBD may be influencing AMPK pathway in maintaining mitochondrial bioenergetics.

Results

Isolation and Characterization of Human Umbilical Cord Mesenchymal Stem Cells Derived Extra Cellular Vesicles (EVs)

Figure 1:
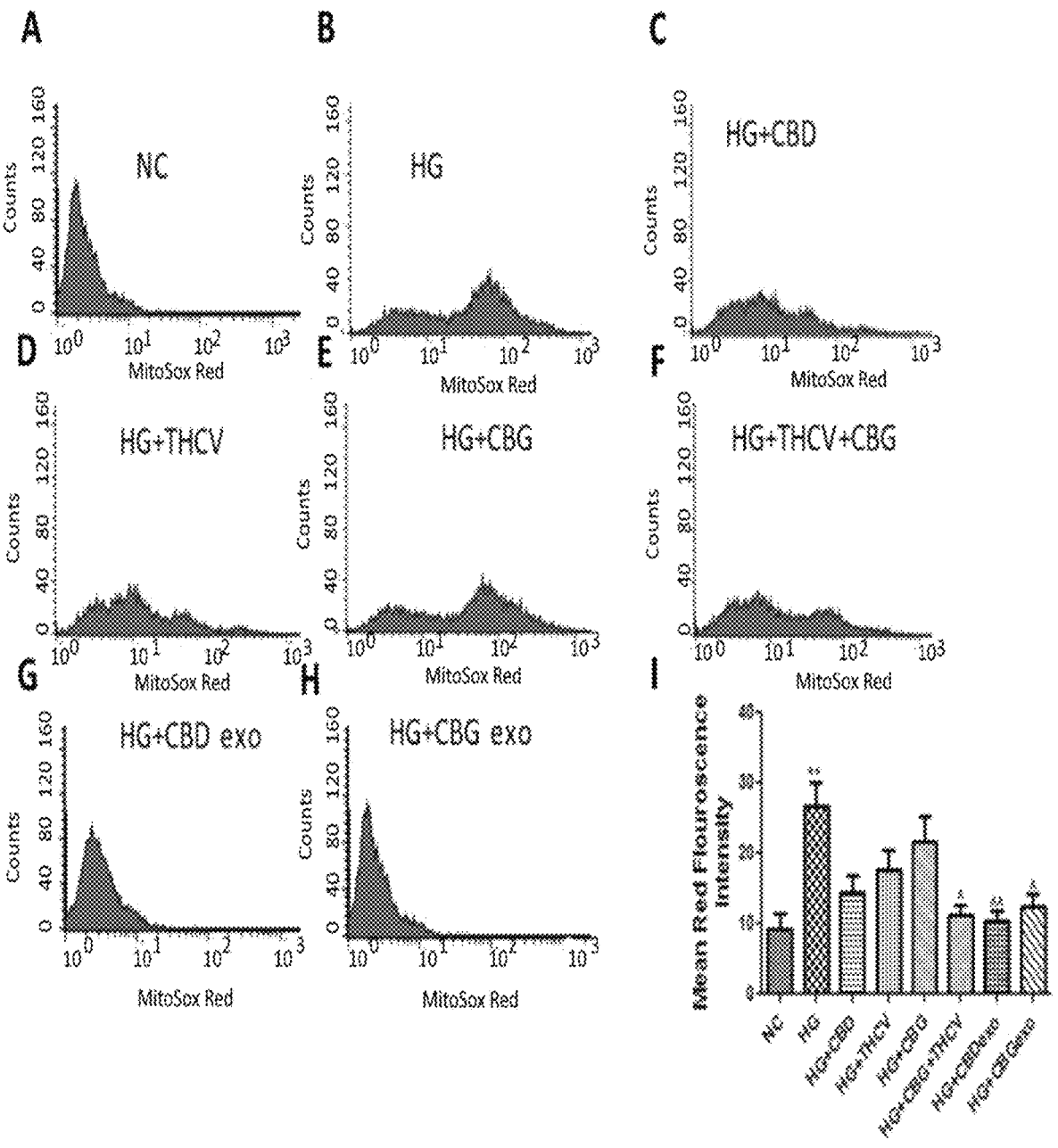
FIG. 1A-I are a series of graphs depicting the effect of synthetic cannabinoids in combination and exosomal formulations on Mitochondrial Superoxides (A) to (H) represents the flow cytometric histograms showing the red fluorescence shift on the X-axis and (I) Bar graph represents the mean red fluorescence intensities in terms of geo means generated data from flow cytometer in different groups. Results are expressed as mean±SEM (n=3). p<0.01 & *P<0.001 Vs NC & ^p<0.05, ^^p<0.01 and ^^^p<0.001 Vs HG.
Figure 2:
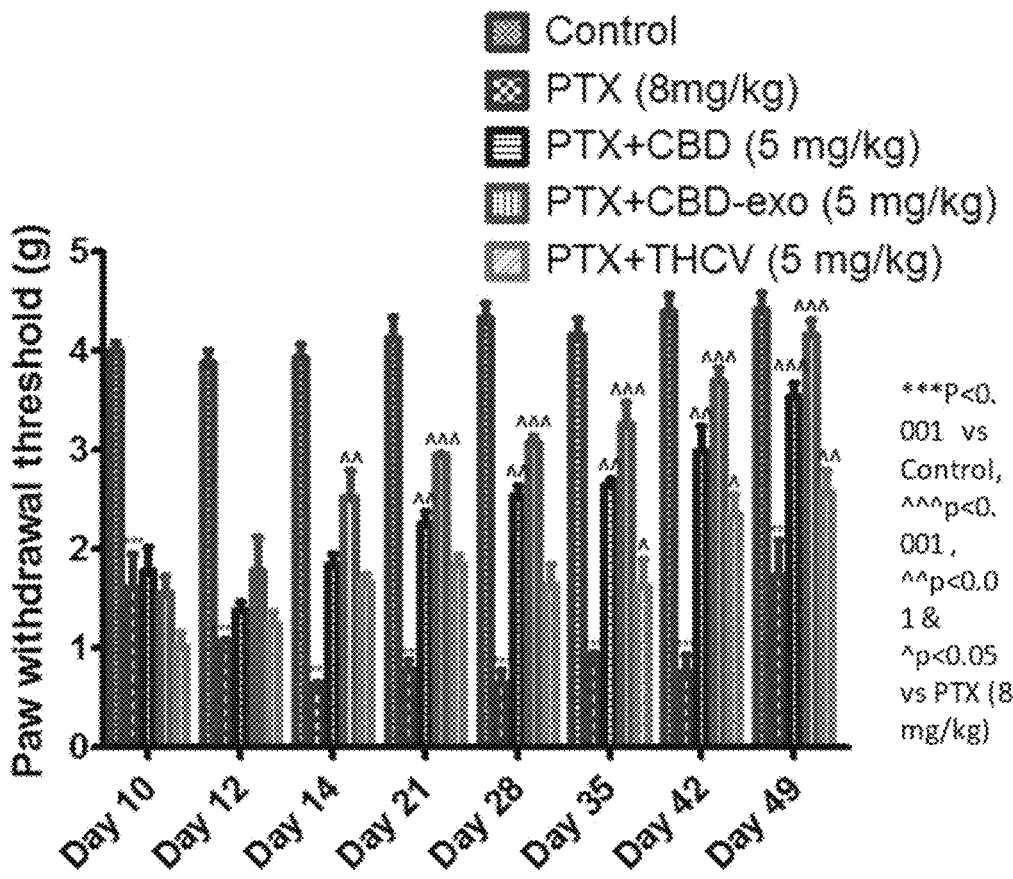
FIG. 2 is a graph depicting paw withdrawal threshold as observed for C57 mice which were initially treated with Paclitaxel (8 mg/kg) for 4 injections every other day. The animals were then treated with CBD 5 mg/kg, THCV 5 mg/kg and also CBD exosomes. CBD exosomes showed the most effect on the neuropathic response as compared to other agents.
Figure 3:
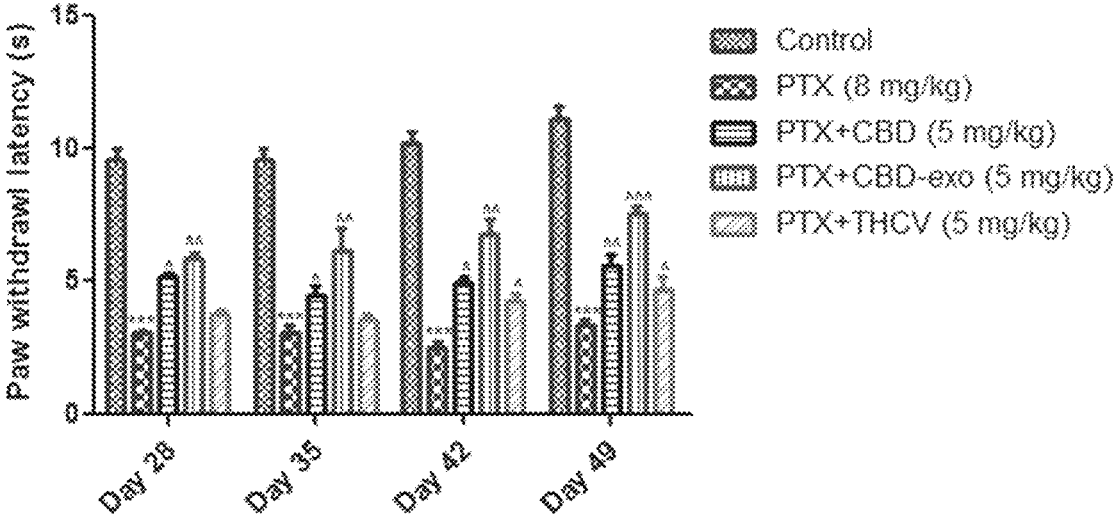
FIG. 3 is a graph depicting paw withdrawal latency as observed for C57 mice after treatment with Paclitaxel, 8 mg/kg for four injections. CBD and THCV at a dose of 5 mg/kg were given to animals. Also exosomes containing 5 mg of CBD (CBD exo) were given to animals which had the most significant response in paw withdrawal latency as a behavioral parameter.
Figure 4:
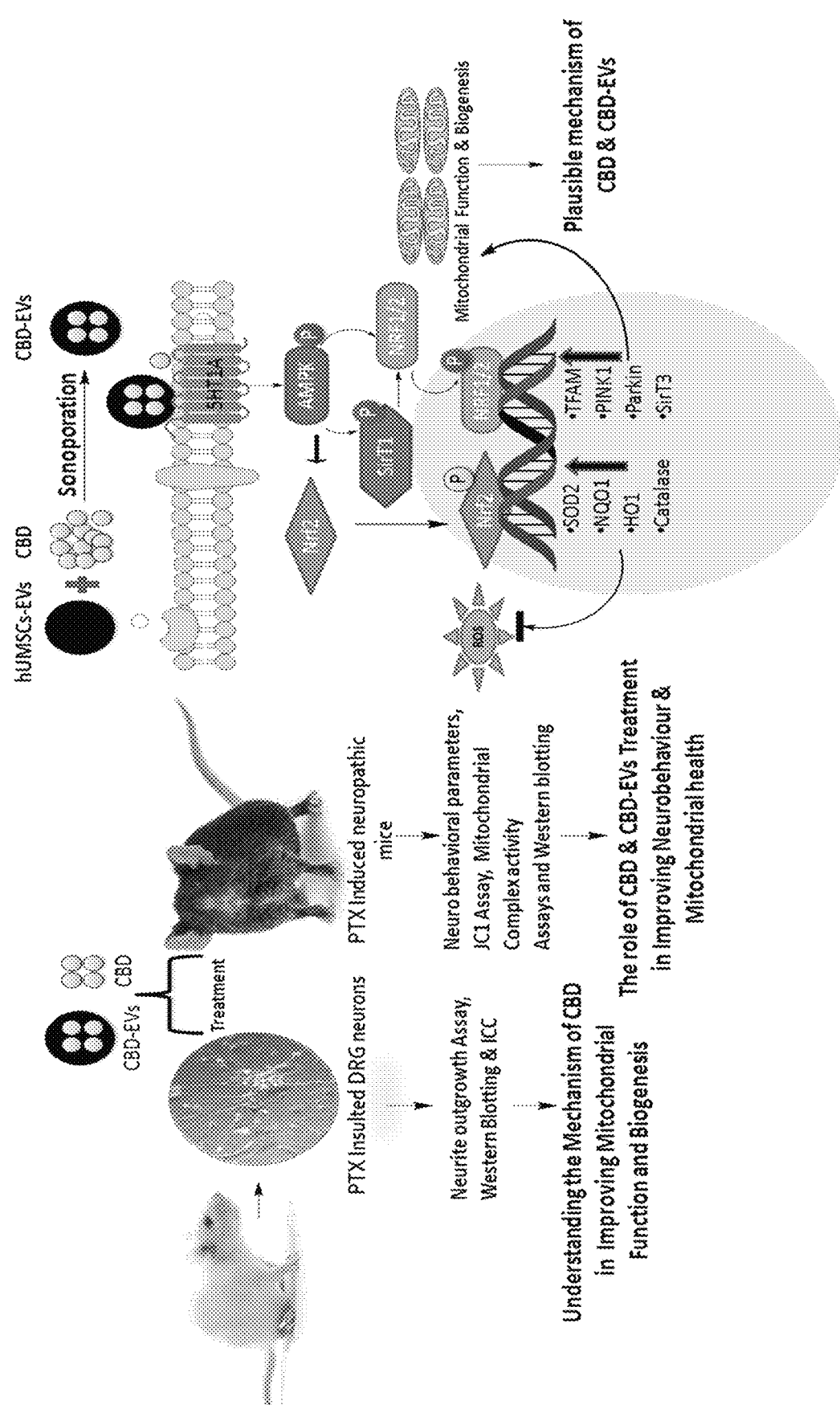
FIG. 4 is an image of the experimental plan. Cannabidiol-Extracellular vesicle (derived from human umbilical cord stem cells) formulation (CBD-EVs) and cannabidiol (CBD) were evaluated against Paclitaxel induced neuropathy in mice and cultured rat dorsal root ganglions. In the mouse model, neurobehavioral studies, mitochondrial functional parameters and western blotting analysis (using DRG and spinal homogenates) was performed. In DRG primary cultures, mechanism of CBD was evaluated using compound C (AMPK inhibitor) by targeting mitochondrial function and mitochondrial biogenesis. CBD-EVs formulation was made by using sonoporation technique and was found to activate AMPK pathway in regulating oxidative stress and mitochondrial function against PTX induced peripheral neuropathy.
Figure 5C:
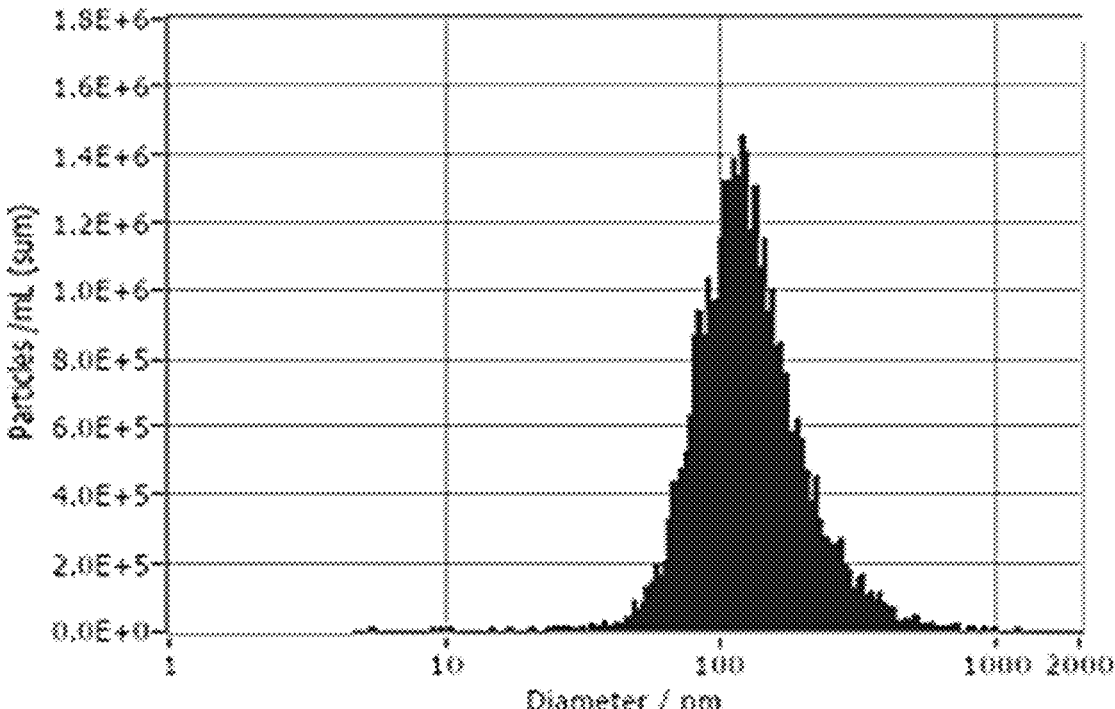

The isolation of EVs from media collected from hUCMSCs cultures grown in the 0.1 L PBS-VW bioreactor using a modified differential centrifugation method with PEG precipitation was successful as reported previously [21]. Cytodex 1 microcarrier was used to facilitate the growth of the hUCMSCs in the bioreactor by acting as a support matrix. The mean particle size, average particle number and zeta potential of the isolated EVs were $141.4 \pm 2.1$ nm, $3.6 \times 10^{10}$ particles/ml, $-21.29 \pm 0.66$ mV respectively. The average protein concentration obtained by using the BCA assay kit was approximately 1.1 mg/ml. Consequently, isolated total proteins from hUCMSCs lysates and EVs homogenates are resolved in SDS PAGE gel electrophoresis. Tetraspanins like CD 63, and CD 81 which are considered as exosomal markers increased two- to four-fold ($p<0.001$) in protein lysates obtained from EVs when compared to hUCMSCs cell lysates (FIG. 5A-bB). Other exosomal markers, flotillin 2 and alix were also significantly ($p<0.001$) increased in EVs lysates when compared to hUCMSCs lysates as shown in FIG. 5A-B. Further, the inventors also probed for exosomal negative marker calnexin which significantly ($p<0.05$) increased in hUCMSCs lysates when compared with EVs protein lysates (FIG. 5A-B).

The CBD was loaded into EVs via the optimized sonication method consisting of bovine serum albumin (BSA) pH 7.4, 10% w/w sucrose, with sonication conditions (3 cycles of 30 s on/off, 20% Amplitude (Amp), for a total of 2 min out of 5 min-cooling period between each cycle), followed by incubation at 22/37° C. for 1 h. The mean particle size of EVs loaded with 10% w/v CBD after sonication was $131.9 \pm 1.1$ nm (FIG. 5C) and entrapment efficiency of $92.3 \pm 2.21\%$ and zeta potential of $-30.26 \pm 0.12$ mV.

In Vitro Drug Release from CBD Loaded EVs

Figure 5D:
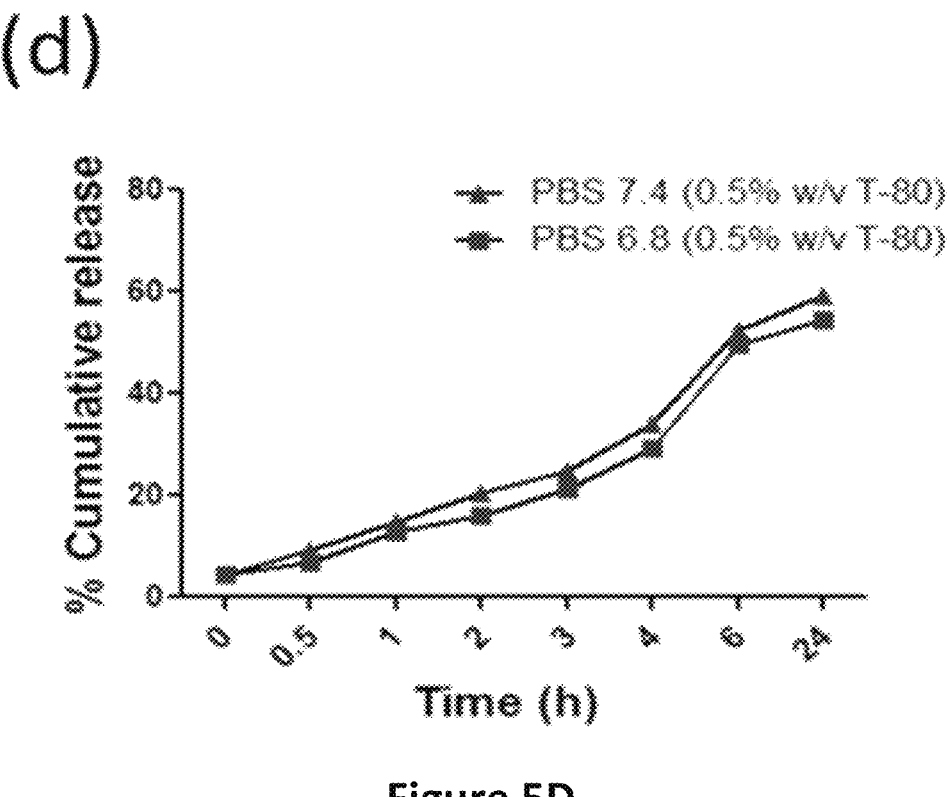

The in vitro drug release experiments for CBD loaded EVs (100 µg/mL) was performed by a dialysis method with cellulose acetate dialysis tubing at pH 6.8 and 7.4 in PBS. At both pH conditions, CBD depicted a sustained release in 24 hours. From FIG. 5D, the percent cumulative release of CBD after 24 hours at pH 6.8 and 7.4 were $50.74 \pm 2.44\%$ and $53.99 \pm 1.4\%$ respectively.

Effect of CBD and CBD Loaded EVs on Neurobehavior of PTX Treated Mice

Tail and paw withdrawal latencies to thermal stimuli were significantly reduced in six weeks after induction of neuropathy by PTX administration in hot water immersion test ($p<0.001$) and Hargreaves plantar test ($p<0.001$) when compared to control animals. These decreases in tail flick and paw withdrawal latencies with hot stimulus and IR radiation respectively were significantly reversed when treated with CBD ($p<0.05$ & 0.01 vs. PTX group) and CBD-EVs ($P<0.01$ & 0.001 vs. PTX group) at 5 mg/kg dose (FIG. 6A-B). Paw withdrawal response of PTX induced neuropathic mice towards mechanical stimuli was assessed through electronic Von Frey and Randall-Selitto pincture. Paw withdrawal threshold ($2.73 \pm 0.24$ g vs. $4.42 \pm 0.15$ g) ($p<0.001$) and paw withdrawal pressure ($84.47 \pm 8.72$ g vs. $171.05 \pm 5.69$ g) ($p<0.001$) were significantly reduced in PTX treated animals when compared to the normal age matched control mice (FIG. 6C-D). These mechanical neurobehavioral changes were corrected by CBD ($p<0.05$) and CBD-EVs ($p<0.01$)

administration at 5 mg/kg dose (FIG. 6C-D). These results indicate that CBD loaded EVs are superior to CBD alone treatment in correcting the neurobehavior of the animals after PTX administration. Moreover, CBD treatment in presence of 5HT1A blocker (WAY100135, 1 µM) did not improve the mechanical and thermal hypersensitivity in PTX treated mice. Also, CBD had no change in neurobehavior with CB1 receptor blocker (rimonabant, 1 µM) as shown in FIG. 6.

Effect of CBD and CBD Loaded EVs on AMPK Pathway

AMPK is considered as bioenergetic sensor which regulates bioenergetic pathways which help in maintaining cellular homeostasis. Western blot analysis revealed that phospho AMPK (p-AMPK) was significantly ($p<0.001$) reduced in DRG and spinal homogenates of PTX induced neuropathic mice when compared to age matched normal control group (FIG. 7). Further, expressions of p-AMPK positively regulated proteins SIRT1, GABP Alpha, TFAM, SOD2, NQO1, PINK1 and HO1 were significantly ($p<0.001$) decreased and negatively regulated NFκB protein expression was significantly increased in DRG homogenates of PTX treated mice when compared to age matched normal control group (FIG. 7). Interestingly, these protein expressions recovered after treatment with CBD and CBD-EVS at 5 mg/kg dose as shown in FIG. 7.

Additionally, spinal homogenates also displayed significantly reduced protein expressions of SOD2 ($p<0.001$), Parkin ($p<0.001$), SIRT1 ($p<0.001$), SIRT3 ($p<0.05$) and catalase ($p<0.05$) in PTX treated mice. CBD and CBD-EVs treatment significantly increased the expressions of these proteins as shown in FIG. 8A-B. However, CBD-EVs treatment was found to be more significant in normalizing these protein expressions when compared with CBD alone treatment in PTX induced neuropathic mice. CBD also increased the expression of 5HT1A receptor significantly in DRG homogenates of PTX treated mice (FIG. 8C-D).

Effect of CBD and CBD Loaded EVs on Mitochondrial Function in DRG and Spinal Homogenates of PTX Treated Mice ATP and NAD+ levels were significantly ($p<0.001$) reduced in isolated fresh DRG and spinal homogenates of PTX treated neuropathic mice (FIG. 9). However, CBD-EVs treatment significantly ($p<0.001$) increased these levels in DRG and spinal homogenates of PTX treated mice (FIG. 9). In comparison, CBD treatment showed significant ($p<0.01$) increase of NAD+ levels in DRG homogenates (FIG. 9B) and ATP levels in spinal homogenates (FIG. 9D) of PTX treated mice. Further, fluorescence assay carried out in dissociated DRG primary cells isolated from mice (L1-L5 region) using mitoprobe JC1 assay kit, demonstrated mitochondrial membrane repolarization effects with CBD and CBD-EVS treatment as shown by concentration dependent formation of red fluorescent J1 aggregates in DRG mitochondria (PTX treated mice, FIG. 9C). This data shows that CBD-EVs have a superior mitoprotective effect as compared to CBD treatment alone.

AMPK Dependent Neuroprotective Effects of CBD in PTX Treated Primary Rat DRG Neurons The inventors examined the neuroprotective effects of CBD in presence of compound C (dorsomorphin dihydrochloride, Sigma, USA), a potent AMPK inhibitor (Ki=109) to conform the CBD dependent effects on AMPK pathway in DRG primary cultures. The number of neurite outgrowths/axon-like extensions which were double/more than the diameter of cell body were noted. The neurite outgrowths and percentage of neurite bearing cells were significantly (p<0.001) reduced in PTX treated DRG cells when compared to untreated DRG cells (FIG. 10).

CBD and CBD-EVs treatment significantly (p<0.001) improved the neurite outgrowth and percentage of neurite bearing cells when compared to PTX treated primary DRG cells. Interestingly, CBD treatment failed to improve the neurite outgrowths in PTX treated primary DRG cells after treatment with compound C (FIG. 10). Moreover, immuno-cytochemistry analysis in DRG Primary cultures also revealed significantly (p<0.001) reduced expressions of p-AMPK and TFAM when treated with PTX at 3 μM for 48 hours (FIG. 11A-B). CBD and CBD-EVs treatment at 12 μM significantly increased the expressions of p-AMPK and TFAM in PTX insulted primary DRG neurons (FIG. 11A-B). However, CBD failed to increase these protein expressions in presence of 10 μM compound C in PTX insulted primary DRG neurons (FIG. 11A-B).

The inventors also studied the downstream signaling of AMPK in the presence of compound C by performing western blotting. The expressions of p-AMPK, SirT1, HO-1, NRF1, TFAM and Catalase were not altered in the PTX+CBD+CC treated group when compared to PTX group but these proteins were significantly increased in CBD and CBD-EVS treated primary DRG homogenates (FIG. 11C-D). These results indicate that neuroprotective and mitoprotective effects of CBD could depend upon the activation of AMPK.

In summary, the inventors found that extracellular vesicles derived from human umbilical cord blood stem cells encapsulated with CBD through sonication are stable for several months at 4° C. CBD-EVs formulation has superior neuroprotective role than CBD alone treatment against paclitaxel induced peripheral neuropathy in rodents. CBD-EVs and CBD protected mitochondrial function by regulating AMPK pathway. CBD stimulates 5HT1A receptors and thereby offers neuroprotection against Paclitaxel induced peripheral neuropathy in mouse.

Materials and Methods hUCMSCs Culture in PBS-Vertical Wheel Bioreactors hUCMSCs culture in PBS-vertical wheel bioreactors hUCMSCs of passage 0 to 2 were acquired from Dr. David Meckes, FSU-College of Medicine Florida State University. In the inventor's previous article, the culture of hUCMSCs for EVs isolation was optimized in PBS-vertical wheel (PBS-VW) bioreactors[21]. Human umbilical cord derived mesenchymal stem cells (hUCMSCs) were cultured in extracellular vesicle-free complete culture medium comprised of α-MEM with 10% EV free FBS, sodium bicarbonate and 1% Penicillin/Streptomycin. At about 80-90% confluence, the cells were detached with Trypsin-EDTA for bioreactor experiments. Approximately 1100-1500 cells/cm² were seeded in a 0.1 L PBS-VW bioreactor along with 0.25 g of cytodex-1 as micro carriers. At the initial stage of seeding the cells, 60 ml of medium was used and for 12 cycles in 4 hours, the speed was set to 25 rpm for five minutes and stationary state for 15 mins. The modified differential centrifugation method involving polyethylene glycol precipitation was used to isolate small EVs from cell-conditioned medium. EVs were characterized by size and zeta potential using ZetaView® BASIC NTA-Nanoparticle Tracking Video Microscope PMX-120, ZetaView software (version 8.05.11 SP4). Western blotting was used to determine the expression of gold standard extracellular vesicle markers such as CD81, CD 63, alix, and flotillin-2 according to the guidelines by minimal information for studies of EVs[55,56].

Preparation of Optimized CBD Loaded Extracellular Vesicles and Characterization

An optimized method for the preparation of CBD-EVs developed in the lab was used 21. Briefly, a previously standardized sonication method was used for the loading of CBD into EVs. Blank EVs ($1.5 \times 10^{11}$ particles/mL) were incubated with 10% w/w (with regards to the protein content) CBD solution and subjected to different sonication cycles (20% Amplitude, 3 cycles of 30 s on/off for 2 min, 5 min-cooling between each cycle). EVs were stabilized with 0.1% (w/v) BSA and along with 10% sucrose solution was to obtain a stable formulation with no precipitation. The formulation was assessed for physical appearance, size, particle number, zeta potential by nanoparticle tracking analysis[17]. The entrapment efficiency was assessed by ultra-filtration method using Vivaspin® 500 centrifugal filter unit (Sartorius, USA) and RP-HPLC analysis as reported previously[22].

Release Studies

Modified dialysis bag method was used to investigate the invitro drug release as per previously described method elsewhere[21]. Briefly, 100 μg/mL of CBD was loaded in EVs and sealed them in an activated dialysis membrane pouch (12 kDa). Further, this pouch was placed in a closed tube containing 10 mL of PBS media with 0.5% tween 80 at pH 6.8 and 7.4. The entire setup was kept in shaker bath maintaining 120 rpm at 37° C. At different time intervals, 1 mL of sample was withdrawn and replaced with fresh medium to achieve sink conditions and further analyzed CBD content by using RP-HPLC method.

Animals

C57BL/6J female mice (4-5 weeks age) and Male Sprague Dawley rats (7-8 weeks age) were obtained from Envigo (Indianapolis, IN) and were used to conduct peripheral neuropathy studies. Florida Agricultural and Mechanical University has AAALAC accredited animal facilities, and all the animal experiments carried out were reviewed and approved by the Institutional Animal Use and Care Committee of Florida Agricultural and Mechanical University (protocol numbers: 020-06 & 021-04) in compliance with NIH guidelines (Guide for the care and use of laboratory animals). All mice and rats were euthanized via exposure to carbon dioxide (CO2).

Briefly, animals were divided into following groups (n=6/group): a. Normal Control: Age matched untreated mice, b. Paclitaxel (PTX) group: 8 mg/kg of PTX administered (i.p.) every other day for four injections), c. Paclitaxel (PTX)+Cannabidiol (CBD): 8 mg/kg of PTX administered (i.p.) every other day for four injections and 5 mg/kg of CBD (i.p) twice a week for total six weeks after last dose of PTX injection, d. Paclitaxel (PTX)+Cannabidiol EVs (CBD-EVs): 8 mg/kg of PTX administered (i.p.) every other day for four injections and 5 mg/kg of CBD loaded in hUCMSCs derived EVs (i.p) twice a week for total six weeks after last dose of PTX injection. After conforming neuropathy in the mice, the neurobehavioral changes of the animals in the different groups were assessed twice in a week for total 42 days. At the end of the experiments, the animals were sacrificed spinal cords and dorsal root ganglions were isolated from L1 to L5 region of spinal cord followed biochemical and molecular assessments. The experimental design and dose of the CBD was selected based on the previous reports 17, 23.

Dorsal Root Ganglions (DRG) Primary Cultures

All neuronal cultures were prepared from (200-250 g) Sprague Dawley rats aging 7-8 weeks and DRGs were dissociated using previously reported methods with slight modifications[24].

Under sterile conditions, DRGs with roots ((L1-L5); 25-30/Rat) were collected in F-12 (Hams-F 12) medium supplemented with 10% Fetal bovine serum and ganglia were carefully removed from roots and capsular connective tissue. The tissue was incubated with collagenase (0.125%) for 1½ hours followed by centrifugation (1200 rpm, 2 mins) and then trypsin (0.25%) incubation for 30 mins and triturated with glass pipette to dissociate into cells. Trypsin was deactivated by adding 20% FBS and then suspension was filtered through a 70 μM nylon gauge and centrifuged at 1200 rpm for 5 mins, supernatant was removed and the cell pellet was resuspended in primary neuron basal media (cat #CC-3256, LonZa, MD, USA) containing primary neurons supplement (cat #CC-4462, LonZa, MD, USA). Single rat DRGs isolated were used to make two 24 well plates with 10,000 cells/well. The 24 well plates were coated with 50 μl of matrigel and wrapped over the bottom of the plate and dried for 1 hour in laminar hood before plating the cells.

Neurite Outgrowth Assay

A 24-well plate seeded at a density of 10000 DRG cells/well was exposed to 3 μM of PTX followed by post treatment with CBD and CBD-EVs at (12 μM each) for 48 hours. Five fields were selected randomly and examined with phase contrast microscope (Nikon ECLIPSE, Ti-U, Japan). Image J software (NIH, USA) was used to measure the length of neurite outgrowths in 30 cells of each chosen field. The number of neurite outgrowths/axon like extensions which are double/more than the diameter of cell body were noted[65]

Immunocytochemistry

Dissociated rat DRG primary cells were plated at a seeding density of 5000 cells/well on glass cover slips placed in 6-well plates. Post 48 hours treatment, media was removed and the cells were washed with PBST thrice and then the cells were fixed in 4% paraformaldehyde solution for 15 min. Before blocking with 3% BSA for 2 h, cells were permeabilized with 0.5% Triton-X 100 for 15 min at room temperature. After blocking, DRG primary cells were incubated with primary antibodies; anti rabbit p-AMPK (1:100) and anti-mouse TFAM (1:100) in 3% BSA at 4° C. overnight. Next day, cells were washed with PBST and incubated with secondary anti rabbit antibody conjugated with rhodamine and anti-mouse Alexa488 (Santa Cruz Biotechnology Inc., CA, USA) for 2 h at room temperature. Finally the Coverslips were mounted over the glass slide using DAPI mounting medium (Fluoroshield™, Sigma). Images were captured using a confocal microscope (Leica TCS SP8 Laser Scanning Spectral Confocal microscope, Germany)[63].

Biochemical and Molecular Parameters

Estimation of ATP Levels

ATP levels in DRG tissue homogenates were estimated according to the manufacturer's kit protocol (calorimetric assay, MAK190, Sigma). The concentration of ATP was expressed in nmol/mg protein as previously reported[61].

Estimation of NAD$^+$ Levels and NADH Levels

NAD$^+$/NADH levels in the fresh DRG homogenates were measured according to manufacturer's protocol (Sigma Aldrich, MO, USA). The concentration of NAD$^+$ levels was expressed in nanograms/mg protein as described earlier[59].

JC1 Assay

JC-1 Staining was performed on dissociated fresh DRG cells as described earlier[62,63]. Dissociated DRG cells were incubated for 30 min with 5 μM of JC-1. The suspension was centrifuged at 3000 rpm for 5 mins at 37° C., the pellet was resuspended in PBS. Subsequently, 200 μl of PBS was added to each black well and the red fluorescence was measured at ~590 nm using the Infinite M200 multi-plate reader (Tecan, Austria). The relative fluorescence intensity measured was normalized with protein concentration and represented as % fluorescence intensity with respect to the control group.

Western Blotting

DRG and spinal cord tissue protein homogenates were prepared in tissue protein extraction reagent (TPER, Sigma) and DRG primary cell lysates and hUCMSCs and hUCMSCs-EVs lysates were prepared in radioimmunoassay buffer (RIPA) containing 1:100 protease and phosphatase inhibitors. The tissue and cellular homogenates were centrifuged at 10,000 g for 20 min at 4° C. and the supernatants were collected and the protein content was determined using bicinchonic acid assay kit. Briefly, 40 μg of protein samples were loaded and resolved by using SDS-PAGE gel electrophoresis and transferred on to the PVDF membrane using Transblot "Turbo" transfer system (semi-dry transfer unit, BIORAD, USA) followed by blocking with 5% BSA solution in PBST. After blocking, The PVDF membranes were incubated with primary antibodies at 4° C. overnight; AMPK, p-AMPK, SIRT1, NRF2, NRF1, SOD2, SIRT3, 5HT1A and Parkin (Cell signaling technology), Flotillin-2, CD 63, CD81, Alix, Calnexin, Catalase, TFAM, HO-1, CB1 and NQO1 (Santacruz biotechnologies, CA) were prepared at 1:1000 dilution in PBST. The membranes were incubated with HRP conjugated secondary anti-rabbit and anti-mouse antibodies for 2 h at room temperature. Luminescence signal was captured using a ChemiDoc™ MXRS$^+$ imaging system (BIO-RAD) and the obtained band intensities were quantified by using image J software (version 1.48, NIH, USA)[64].

Behavioral Parameters

Thermal and Mechanical Hyperalgesia

Thermal hyperalgesia in mice was measured by using Hargreaves plantar test and tail immersion method as described earlier[57,58].

Plantar Test (Hargreaves Method)

Prior to the experiment, the animals were acclimatized for 1 hour on heated base (30° C.) horizontal glass surface covered with plexiglass boxes which can accommodate 12 mice at a given time. Using test head and radiant heat source, time taken for a mouse to lift the paw when infrared irradiation (40 IR units) exposed was recorded with a cut off time of 20 s and five consecutive readings were recorded by giving 10 mins time gap and each reading reported as paw withdrawal latency in seconds.

Hot Immersion Test

Thermal hyperalgesia of the mice was also measured using hot (55° C.±0.5) test in which the time latency for the animal to flick its tail was measured with cut off time 20 s and three consecutive readings were taken with an interval of 10 mins among each reading and reported as paw withdrawal latency in s.

Electronic Vonfrey Test and Randall Selitto Test

Electronic Vonfrey measures the force at which paw withdrawal of the mice in grams indicating paw withdrawal threshold. Five consecutive readings were taken with at least 10 min interval among each read point. The average of the paw withdrawal threshold was calculated from the five observations per animal. Randall Selitto pincture pressure was applied on both paws and paw withdrawal time point was recorded with difference of 10 min in recording between two consecutive readings. The average of five readings per animal was reported as paw withdrawal pressure in seconds[59,60].

Statistical Significance

One way analysis of variation (ANOVA) was used to compare between the groups, followed by post hoc analysis using Bonferroni's Multiple Comparison Test in GraphPad prism software. Two-way ANOVA was used to compare more than two factors followed by Bonferroni's Multiple Comparison Post Test. All data was analyzed in consultation with a statistician and considered at p<0.05 as statistically significant.

Conclusion

In summary, the inventors found that CBD-EVs prepared from sonication method has shown potential in reducing mechanical and thermal pain sensitivities which are superior to CBD alone against PIPN in mice. CBD and CBD-EVs have a potent mitoprotective effects in neuronal cells via activating 5HT1A receptors and AMPK pathway. CBD was shown to depend on AMPK activation in improving mitochondrial function and biogenesis against PIPN both in in vitro and in vivo.

Example 3—Treatment of Diabetic Neuropathy

Diabetic neuropathy is a chronic devastating complication which can approximately affects 50-60% of the diabetic subjects. Distal symmetric polyneuropathy is the core manifestation of the diabetes which results in hyperalgesia, burning pain in the limbs which if ignored can develop into foot ulcers. Oxidative stress and neuroinflammation are found to be the preponderant mechanisms of hyperglycemia induced neuronal damage. These factors may underlie the peripheral sensitization of nociceptors, demyelination, endothelial damage and can cause hyperalgesia, conduction velocity and blood flow deficits respectively.

Medical marijuana provides symptomatic relief clinically for pain associated with diabetic peripheral neuropathy (DPN). In diabetic patients, nerve injury is a common complication that leads to chronic pain, numbness and substantial loss of quality of life. The non-psychoactive minor phytocannabinoids, Cannabidiol (CBD), Cannabigerol (CBG) and Tetrahydrocannabivarin (THCV) have shown their potential in reducing neuropathic and musculoskeletal pain by regulating inflammation and oxidative stress via antagonizing CB1 receptors and agonizing CB2 receptors and transient receptor potential cation channel subfamily V member 1 (TRPV1) ion channels.

The inventors identified the transcriptomic signatures of Cannabidiol (CBD) and tetrahydro-cannabivarin (THCV) in Streptozotocin induced experimental diabetic neuropathy (DN). THCV reduced obesity and diabetes in rodent studies by acting as a direct antioxidant through functioning as a neutral antagonist for CB1 receptors and partial agonist for CB2 receptors. CBD was under clinical trials for the indication of diabetes and diabetic complications, however the phytocannbinoids pharmacological mechanisms were not well explored.

Animals were rendered diabetic using STZ (55 mg/kg, i.p). CBD was administered (10 & 20 mg/kg, i.p) and THCV (15 & 30 mg/kg, i.p) during the last 4 weeks of 12 week diabetic period. The animals' pain perception was assessed using the Hargreaves plantar test, hot and cold plate method, Vonfrey aesthesiometer, and Randal Sellito apparatus, and nerve functional assessment using the Laser Doppler oxymeter. After the study, the animals' blood was drawn to measure blood glucose levels and their DRGs were isolated for transcriptomic studies.

The inventors found that diabetic animals after eight weeks significantly (P<0.001) increased hypersensitivity to thermal and mechanical pain and also significantly (p<0.001) reduced nerve blood flow when compared to the age matched control animals. CBD and THCV treatment reversed these effects in a dose-dependent manner while having no effect on the animals' body weights or blood glucose levels. Differently expressed genes (transcriptomic analysis) have been discovered in the isolated DRGs of control, diabetic, and treated animals, with 32 genes in the control group, 33 in the THCV group, and 45 in the CBD group, all of which differ from the genes expressed in diabetic animals' DRGs. These genes regulating nerve function by affecting the RAP1 signaling pathway, MAP kinase signaling pathway, neurotrophin signaling pathway, Parkinson's disease, Alzheimer's disease, focal adhesion, insulin signaling pathway, mi-croRNAs in cancer, and others according to KEGG analysis.

Conclusion

Despite the fact that CBD and THCV are non-psychoactive medical marijuana components, they differ in their ability to regulate different genes that contribute to the health of neurons in diabetic condition. CBD and THCV showed neuroprotective benefits in diabetes-induced neuropathic rats, as measured by a variety of neurobehavioral and nerve functional characteristics. MAP kinase, Insulin, Rap1, Neurotropin, TNF, Apelin, FoXO, and ErbB signaling pathways, along with Micro-RNAs, were found to be involved in the pathogenesis of diabetic peripheral neuropathy by transcriptome analysis of DRG homogenates from diverse treatment groups of rats.

Example 4—Method of Treating
Chemotherapy-Induced Neuropathy (Prophetic)

A 48-year-old woman is diagnosed with breast cancer. She undergoes chemotherapy with the drug paclitaxel being administered once per week. After being on paclitaxel for a period of time, the patient begins exhibiting signs of CIPN. Symptoms include pain, tingling sensations, burning, decreased sensation, and weakness. A composition comprised of a plurality of CBD encapsulated exosomes is prepared according to the procedures described in Example 2. Briefly, EVs are derived from human umbilical cord mesenchymal stem cells. Blank EVs ($1.5 \times 10^{11}$ particles/mL) are incubated with 10% w/w (with regards to the protein content) CBD solution and subjected to different sonication cycles (20% Amplitude, 3 cycles of 30 s on/off for 2 min, 5 min-cooling between each cycle). EVs are stabilized with 0.1% (w/v) BSA and along with 10% sucrose solution a stable formulation with no precipitation is obtained. The patient is administered, via i.p. injection, a therapeutically effective amount of the composition for a time sufficient alleviate the CIPN symptoms. The symptoms do not return.

Example 5—Method of Treating Diabetic Induced
Neuropathy (Prophetic)

A 60-year-old diabetic man presents with tingling and burning sensations, numbness and muscle weakness in his extremities. He is diagnosed with diabetic peripheral neuropathy. A composition comprised of a plurality of CBD encapsulated exosomes is prepared according to the procedures described in Example 2. Briefly, EVs are derived from human umbilical cord mesenchymal stem cells. Blank EVs ($1.5 \times 10^{11}$ particles/mL) are incubated with 10% w/w (with regards to the protein content) CBD solution and subjected to different sonication cycles (20% Amplitude, 3 cycles of 30 s on/off for 2 min, 5 min-cooling between each cycle). EVs are stabilized with 0.1% (w/v) BSA and along with 10% sucrose solution a stable formulation with no precipitation is obtained. The patient is administered via i.p. injection a therapeutically effective amount of a composition comprised of a plurality of CBD encapsulated exosomes for a time period sufficient to alleviate his symptoms. The symptoms do not return.

A 67-year-old diabetic woman presents with tingling and burning sensations and numbness in her extremities. She is diagnosed with diabetic peripheral neuropathy. A composition comprised of a plurality of THCV encapsulated exosomes is prepared. Briefly, EVs are derived from human umbilical cord mesenchymal stem cells. Blank EVs (1.5× $10^{11}$ particles/mL) are incubated with 10% w/w (with regards to the protein content) THCV solution and subjected to different sonication cycles (20% Amplitude, 3 cycles of 30 s on/off for 2 min, 5 min-cooling between each cycle). EVs are stabilized with 0.1% (w/v) BSA and along with 10% sucrose solution a stable formulation with no precipitation is obtained. The patient is administered via i.p. injection a therapeutically effective amount of a composition comprised of a plurality of THCV encapsulated exosomes for a time period sufficient to alleviate her symptoms. The symptoms do not return.

A 70-year-old diabetic man presents with numbness and muscle weakness in his extremities. He is diagnosed with diabetic peripheral neuropathy. A composition comprised of a plurality of a combination CBD and THCV encapsulated exosomes is prepared according to the procedures described in Example 2. Briefly, EVs are derived from human umbilical cord mesenchymal stem cells. Blank EVs (1.5×$10^{11}$ particles/mL) are incubated with an amount of (with regards to the protein content) CBD solution and THCV solution and subjected to different sonication cycles (20% Amplitude, 3 cycles of 30 s on/off for 2 min, 5 min-cooling between each cycle). EVs are stabilized with 0.1% (w/v) BSA and along with 10% sucrose solution a stable formulation with no precipitation is obtained. The patient is administered via i.p. injection a therapeutically effective amount of a composition comprised of a plurality of combination CBD and THCV encapsulated exosomes for a time period sufficient to alleviate his symptoms. The symptoms do not return.

REFERENCES

1. C. Nehate, S. Jain, A. Saneja, V. Khare, N. Alam, R. Dhar Dubey, et al., Paclitaxel formulations: challenges and novel delivery options. Current drug delivery. 2014; 11:666-686
2. H. S. Rugo, W. T. Barry, A. Moreno-Aspitia, A. P. Lyss, C. Cirrincione, E. Leung, et al., Randomized phase III trial of paclitaxel once per week compared with nanoparticle albumin-bound nab-paclitaxel once per week or ixabepilone with bevacizumab as first-line chemotherapy for locally recurrent or metastatic breast cancer: CALGB 40502/NCCTG N063H (Alliance). Journal of Clinical Oncology. 2015; 33:2361
3. R. Zajączkowska, M. Kocot-Kępska, W. Leppert, A. Wrzosek, J. Mika and J. Wordliczek, Mechanisms of chemotherapy-induced peripheral neuropathy. International journal of molecular sciences. 2019; 20:1451
4. T. Postma, J. Vermorken, A. Liefting, H. Pinedo and J. Heimans, Paclitaxel-induced neuropathy. Annals of Oncology. 1995; 6:489-494
5. A. K. Kalvala, V. G. Yerra and A. Kumar, LONP1 induction by SRT1720 attenuates mitochondrial dysfunction against high glucose induced neurotoxicity in PC12 cells. Toxicology in Vitro. 2020; 62:104695
6. P. A. Li, X. Hou and S. Hao, Mitochondrial biogenesis in neurodegeneration. Journal of neuroscience research. 2017; 95:2025-2029

7. A. K. Kalvala, I. Khan, C. Gundu and A. Kumar, An overview on ATP dependent and independent proteases including an anterograde to retrograde control on mitochondrial function; Focus on diabetes and diabetic complications. Current pharmaceutical design. 2019; 25:2584-2594
8. D. E. Brenneman, W. A. Kinney and S. J. Ward, Knockdown siRNA targeting the mitochondrial sodium-calcium exchanger-1 inhibits the protective effects of two cannabinoids against acute paclitaxel toxicity. Journal of Molecular Neuroscience. 2019; 68:603-619
9. K. M. King, A. M. Myers, A. J. Soroka-Monzo, R. F. Tuma, R. J. Tallarida, E. A. Walker, et al., Single and combined effects of A9-tetrahydrocannabinol and cannabidiol in a mouse model of chemotherapy-induced neuropathic pain. British journal of pharmacology. 2017; 174:2832-2841
10. S. C. Britch, S. Babalonis and S. L. Walsh, Cannabidiol: pharmacology and therapeutic targets. Psychopharmacology. 2021; 238:9-28
11. E. Perucca and M. Bialer, Critical aspects affecting cannabidiol oral bioavailability and metabolic elimination, and related clinical implications. CNS drugs. 2020; 34:795-800
12. Í. M. d. M. Ramalho, D. T. Pereira, G. B. L. Galvão, D. T. Freire, L. Amaral-Machado, É. d. N. Alencar, et al., Current trends on cannabidiol delivery systems: Where are we and where are we going? Expert Opinion on Drug Delivery. 2021
13. J. Ren, N. Liu, N. Sun, K. Zhang and L. Yu, Mesenchymal stem cells and their exosomes: Promising therapeutics for chronic pain. Current stem cell research & therapy. 2019; 14:644-653
14. X. Gu, Y. Li, K. Chen, X. Wang, Z. Wang, H. Lian, et al., Exosomes derived from umbilical cord mesenchymal stem cells alleviate viral myocarditis through activating AMPK/mTOR-mediated autophagy flux pathway. Journal of cellular and molecular medicine. 2020; 24:7515-7530
15. Y. Madhavi, N. Gaikwad, V. G. Yerra, A. K. Kalvala, S. Nanduri and A. Kumar, Targeting AMPK in diabetes and diabetic complications: energy homeostasis, autophagy and mitochondrial health. Current medicinal chemistry. 2019; 26:5207-5229
16. J. Mlost, M. Bryk and K. Starowicz, Cannabidiol for pain treatment: focus on pharmacology and mechanism of action. International journal of molecular sciences. 2020; 21:8870
17. S. J. Ward, S. D. McAllister, R. Kawamura, R. Murase, H. Neelakantan and E. A. Walker, Cannabidiol inhibits paclitaxel-induced neuropathic pain through 5-HT1A receptors without diminishing nervous system function or chemotherapy efficacy. British Journal of Pharmacology. 2014; 171:636-645
18. A. M. Polter and X. Li, 5-HT1A receptor-regulated signal transduction pathways in brain. Cellular signalling. 2010; 22:1406-1412
19. S. S. Jain, S. Paglialunga, C. Vigna, A. Ludzki, E. A. Herbst, J. S. Lally, et al., High-fat diet-induced mitochondrial biogenesis is regulated by mitochondrial-derived reactive oxygen species activation of CaMKII. Diabetes. 2014; 63:1907-1913
20. M. B. Hock and A. Kralli, Transcriptional control of mitochondrial biogenesis and function. Annual review of physiology. 2009; 71:177-203
21. N. Patel, N. Kommineni, S. K. Surapaneni, A. Kalvala, X. Yaun, A. Gebeyehu, et al., Cannabidiol Loaded Extracellular Vesicles Sensitize Triple-Negative Breast Cancer to Doxorubicin in both in-vitro and in vivo Models Running Title: Formulation and anti-cancer potential of CBD loaded hUCMSC-derived Extracellular Vesicles in TNBC. International Journal of Pharmaceutics. 2021: 120943

22. N. Kommineni, E. Nottingham, A. Bagde, N. Patel, A. K. Rishi, S. R. Dev, et al., Role of nano-lipid formulation of CARP-1 mimetic, CFM-4.17 to improve systemic exposure and response in osimertinib resistant non-small cell lung cancer. European Journal of Pharmaceutics and Biopharmaceutics. 2021; 158:172-184

23. S. J. Ward, M. D. Ramirez, H. Neelakantan and E. A. Walker, Cannabidiol prevents the development of cold and mechanical allodynia in paclitaxel-treated female C57B16 mice. Anesthesia and analgesia. 2011; 113:947

24. A. Saleh, J. Schapansky, D. Smith, N. Young, G. Odero, B. Aulston, et al., Normalization of NF-κB activity in dorsal root ganglia neurons cultured from diabetic rats reverses neuropathy-linked markers of cellular pathology. Experimental neurology. 2013; 241:169-178

25. C. Bojanic, K. To, B. Zhang, C. Mak and W. S. Khan, Human umbilical cord derived mesenchymal stem cells in peripheral nerve regeneration. World journal of stem cells. 2020; 12:288

26. M. Zhou, M. Hu, S. He, B. Li, C. Liu, J. Min, et al., Effects of RSC96 Schwann cell-derived exosomes on proliferation, senescence, and apoptosis of dorsal root ganglion cells in vitro. Medical science monitor: international medical journal of experimental and clinical research. 2018; 24:7841

27. A. Gebeyehu, N. Kommineni, D. Meckes and M. Sachdeva, Exosome Vehicles as Nano-Drug Delivery Materials for Chemotherapeutic Drugs. Critical Reviews™ in Therapeutic Drug Carrier Systems. 2021

28. Y. Qiu, Y. Yang, R. Yang, C. Liu, J.-M. Hsu, Z. Jiang, et al., Activated T cell-derived exosomal PD-1 attenuates PD-L1-induced immune dysfunction in triple-negative breast cancer. Oncogene. 2021; 40:4992-5001

29. S.-J. Shiue, R.-H. Rau, H.-S. Shiue, Y.-W. Hung, Z.-X. Li, K. D. Yang, et al., Mesenchymal stem cell exosomes as a cell-free therapy for nerve injury-induced pain in rats. Pain. 2019; 160:210-223

30. M. J. Lee, T. G. Yoon, M. Kang, H. J. Kim and K. S. Kang, Effect of subcutaneous treatment with human umbilical cord blood-derived multipotent stem cells on peripheral neuropathic pain in rats. The Korean Journal of Physiology & Pharmacology. 2017; 21:153-160

31. R. Y. North, Y. Li, P. Ray, L. D. Rhines, C. E. Tatsui, G. Rao, et al., Electrophysiological and transcriptomic correlates of neuropathic pain in human dorsal root ganglion neurons. Brain. 2019; 142:1215-1226

32. L. Livni, J. G. Lees, M. E. Barkl-Luke, D. Goldstein and G. Moalem-Taylor, Dorsal root ganglion explants derived from chemotherapy-treated mice have reduced neurite outgrowth in culture. Neuroscience letters. 2019; 694:14-19

33. X. Liu, R. R. Chhipa, I. Nakano and B. Dasgupta, The AMPK inhibitor compound C is a potent AMPK-independent antiglioma agent. Molecular cancer therapeutics. 2014; 13:596-605

34. E. Hao, P. Mukhopadhyay, Z. Cao, K. Erdélyi, E. Holovac, L. Liaudet, et al., Cannabidiol protects against doxorubicin-induced cardiomyopathy by modulating mitochondrial function and biogenesis. Molecular medicine. 2015; 21:38-45

35. Q. Zhou, M. Xie, J. Zhu, Q. Yi, B. Tan, Y. Li, et al., PINK1 contained in huMSC-derived exosomes prevents cardiomyocyte mitochondrial calcium overload in sepsis via recovery of mitochondrial Ca 2+ efflux. Stem cell research & therapy. 2021; 12:1-14

36. X. Li, M. Xu, C. Ma, Y. Lyu and X. Ma, Exosomes derived from human placental mesenchymal stem cells reduce human lung microvascular endothelial cell injury induced by lipopolysaccharide via enhancing autophagy. Xi bao yu fen zi Mian yi xue za zhi=Chinese Journal of Cellular and Molecular Immunology. 2021; 37:225-232

37. R. Gallily, Z. Yekhtin, M. Tarshis and R. V. Sionov, Cannabidiol (CBD) Prevents Palmitic Acid-Induced Drop in Mitochondrial Membrane Potential. Pharmacology & Pharmacy. 2019; 10:387-395

38. K. E. Inyang, T. A. McDougal, E. D. Ramirez, M. Williams, G. Laumet, A. Kavelaars, et al., Alleviation of paclitaxel-induced mechanical hypersensitivity and hyperalgesic priming with AMPK activators in male and female mice. Neurobiology of Pain. 2019; 6:100037

39. B. Kola, M. Christ-Crain, G. Wittman, C. Leontiou, A. Grossman, C. Fekete, et al., 2006. Cannabinoids increase AMP-activated protein kinase (AMPK) enzyme activity in the hypothalamus and heart via different signalling pathways-studies in CB1 knockout animals Endocrine Abstracts, Bioscientifica, 40. X. Li, S. Yang, L. Wang, P. Liu, S. Zhao, H. Li, et al., Resveratrol inhibits paclitaxel-induced neuropathic pain by the activation of PI3K/Akt and SIRT1/PGCla pathway. Journal of pain research. 2019; 12:879

41. S. Kang, J. Li, Z. Yao and J. Liu, Cannabidiol induces autophagy to protects neural cells from mitochondrial dysfunction by upregulating SIRT1 to inhibits NF-κB and NOTCH pathways. Frontiers in cellular neuroscience. 2021; 15:95

42. Y. Quan, Y. Xin, G. Tian, J. Zhou and X. Liu, Mitochondrial ROS-modulated mtDNA: a potential target for cardiac aging. Oxidative medicine and cellular longevity. 2020; 2020

43. N. Larsson, Wang J, Wilhelmsson H, Oldfors A, Rustin P, Lewandoski M, Barsh GS, Clayton DA. Mitochondrial transcription factor A is necessary for mtDNA maintenance and embryogenesis in mice. Nat Genet. 1998; 18:231-236

44. A. Trecarichi and S. J. Flatters, Mitochondrial dysfunction in the pathogenesis of chemotherapy-induced peripheral neuropathy. International review of neurobiology. 2019; 145:83-126

45. S. Atalay, I. Jarocka-Karpowicz and E. Skrzydlewska, Antioxidative and anti-inflammatory properties of cannabidiol. Antioxidants. 2020; 9:21

46. A. A. I. Arbab, X. Lu, I. M. Abdalla, A. A. Idris, Z. Chen, M. Li, et al., Metformin Inhibits Lipoteichoic Acid-Induced Oxidative Stress and Inflammation Through AMPK/NRF2/NF-κB Signaling Pathway in Bovine Mammary Epithelial Cells. Frontiers in Veterinary Science. 2021; 8

47. H. Yuan, Q. Yang, B. Yang, H. Xu, O. Nasif, S. Muruganantham, et al., Phyllanthin Averts Oxidative Stress and Neuroinflammation in Cerebral Ischemic-Reperfusion Injury through Modulation of the NF-κB and AMPK/Nrf2 Pathways. Journal of Environmental Pathology, Toxicology and Oncology. 2021; 40

48. P. Thampi, H. V. Rao, S. K. Mitter, J. Cai, H. Mao, H. Li, et al., The 5HT1a receptor agonist 8-Oh DPAT induces protection from lipofuscin accumulation and oxidative stress in the retinal pigment epithelium. PloS one. 2012; 7:e34468

49. C. H. A. Jesus, D. D. B. Redivo, A. T. Gasparin, B. B. Sotomaior, M. C. de Carvalho, K. Genaro, et al., Cannabidiol attenuates mechanical allodynia in streptozotocin-induced diabetic rats via serotonergic system activation through 5-HT1A receptors. Brain research. 2019; 1715: 156-164

50. D. Pascual, C. Goicoechea, M. Suardíaz and M. I. Martín, A cannabinoid agonist, WIN 55,212-2, reduces neuropathic nociception induced by paclitaxel in rats. Pain. 2005; 118:23-34

51. F. H. Do Monte, R. R. Souza, R. M. Bitencourt, J. A. Kroon and R. N. Takahashi, Infusion of cannabidiol into infralimbic cortex facilitates fear extinction via CB1 receptors. Behavioural brain research. 2013; 250:23-27

52. O. Sagredo, J. A. Ramos, A. Decio, R. Mechoulam and J. Fernández-Ruiz, Cannabidiol reduced the striatal atrophy caused 3-nitropropionic acid in vivo by mechanisms independent of the activation of cannabinoid, vanilloid TRPV1 and adenosine A2A receptors. European Journal of Neuroscience. 2007; 26:843-851

53. T. Bisogno, L. Hanuš, L. De Petrocellis, S. Tchilibon, D. E. Ponde, I. Brandi, et al., Molecular targets for cannabidiol and its synthetic analogues: effect on vanilloid VR1 receptors and on the cellular uptake and enzymatic hydrolysis of anandamide. British journal of pharmacology. 2001; 134:845-852

54. E. M. Blessing, M. M. Steenkamp, J. Manzanares and C. R. Marmar, Cannabidiol as a potential treatment for anxiety disorders. Neurotherapeutics. 2015; 12:825-836

55. A. Cvjetkovic, J. Lötvall and C. Lässer, The influence of rotor type and centrifugation time on the yield and purity of extracellular vesicles. Journal of extracellular vesicles. 2014; 3:23111

56. A. T. Reiner, K. W. Witwer, B. W. Van Balkom, J. De Beer, C. Brodie, R. L. Corteling, et al., Concise review: Developing best-practice models for the therapeutic use of extracellular vesicles. Stem cells translational medicine. 2017; 6:1730-1739

57. A. K. Kalvala, R. Kumar, B. Sherkhane, C. Gundu, V. K. Arruri and A. Kumar, Bardoxolone methyl ameliorates hyperglycemia induced mitochondrial dysfunction by activating the keap1-Nrf2-ARE pathway in experimental diabetic neuropathy. Molecular neurobiology. 2020; 57:3616-3631

58. X. Zang, J. B. Lee, K. Deshpande, O. B. Garbuzenko, T. Minko and L. Kagan, Prevention of paclitaxel-induced neuropathy by formulation approach. Journal of Controlled Release. 2019; 303:109-116

59. V. G. Yerra, A. K. Kalvala and A. Kumar, Isoliquiritigenin reduces oxidative damage and alleviates mitochondrial impairment by SIRT1 activation in experimental diabetic neuropathy. The journal of nutritional biochemistry. 2017; 47:41-52

60. T. Martinov, M. Mack, A. Sykes and D. Chatterjea, Measuring changes in tactile sensitivity in the hind paw of mice using an electronic von Frey apparatus. Journal of visualized experiments: JoVE. 2013

61. A. K. Kalvala, V. G. Yerra, B. Sherkhane, C. Gundu, V. Arruri, R. Kumar, et al., Chronic hyperglycemia impairs mitochondrial unfolded protein response and precipitates proteotoxicity in experimental diabetic neuropathy: focus on LonP1 mediated mitochondrial regulation. Pharmacological Reports. 2020; 72:1627-1644

62. A. Saleh, J. Schapansky, D. Smith, N. Young, G. Odero, B. Aulston, et al., Normalization of NF-κB activity in dorsal root ganglia neurons cultured from diabetic rats reverses neuropathy-linked markers of cellular pathology. Experimental neurology. 2013; 241:169-178

63. A. K. Kalvala, V. G. Yerra and A. Kumar, LONP1 induction by SRT1720 attenuates mitochondrial dysfunction against high glucose induced neurotoxicity in PC12 cells. Toxicology in Vitro. 2020; 62:104695

64. P. Gangadaran, R. L. Rajendran, H. W. Lee, S. Kalimuthu, C. M. Hong, S. Y. Jeong, et al., Extracellular vesicles from mesenchymal stem cells activates VEGF receptors and accelerates recovery of hindlimb ischemia. Journal of Controlled Release. 2017; 264:112-126

65. P. Bheereddy, V. G. Yerra, A. K. Kalvala, B. Sherkhane and A. Kumar, SIRT1 activation by polydatin alleviates oxidative damage and elevates mitochondrial biogenesis in experimental diabetic neuropathy. Cellular and molecular neurobiology. 2020:1-15

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A composition comprising:
(a) exosomes derived from human umbilical cord mesenchymal stem cells (hUCMSCs), the exosomes having a mean particle size of 131.9±1.1 nm and a zeta potential of −30.26±0.12 mV;
(b) cannabidiol (CBD) encapsulated within the exosomes, the CBD having been loaded by sonication at 20% amplitude with three cycles of 30 seconds on and 30 seconds off and a 5-minute cooling interval between cycles;
(c) 0.1% (w/v) bovine serum albumin and 10% (w/w) sucrose present as stabilizers;
(d) a pharmaceutically acceptable carrier; and
(e) the composition exhibits an entrapment efficiency of at least 90% as determined by ultrafiltration with reverse-phase HPLC quantitation.

2. The composition of claim 1, wherein CBD entrapment efficiency is 92.3±2.21% as determined by ultrafiltration with reverse-phase HPLC quantitation.

3. The composition of claim 1, wherein cumulative CBD release at 24 hours is about 50-54% at pH 6.8 and pH 7.4.

4. The composition of claim 1, wherein CBD loading is performed using about 10% w/w relative to exosome protein.

5. The composition of claim 1, wherein the exosomes are characterized by the presence of CD63, CD81, Alix, and Flotillin-2 and by reduced calnexin signal relative to parental hUCMSCs.

6. The composition of claim 1, wherein the exosomes are produced by culturing hUCMSCs in a PBS-vertical-wheel (PBS-VW) bioreactor with microcarriers and isolating extracellular vesicles by polyethylene glycol (PEG) precipitation prior to CBD loading.

7. The composition of claim 1, which is stable without precipitation for several months at 4° C.

8. The composition of claim 1, formulated for parenteral administration.

9. A composition comprising cannabidiol (CBD)-loaded exosomes, wherein:

a) the exosomes are derived from human umbilical cord mesenchymal stem cells (hUCMSCs);

b) the composition comprises 0.1% (w/v) bovine serum albumin and 10% (w/w) sucrose as stabilizers;

c) the CBD is encapsulated within the exosomes in an amount effective to provide an entrapment efficiency of at least 90% as determined by ultrafiltration with reverse-phase HPLC quantitation;

d) the CBD-loaded exosomes have a mean particle size of 131.9±1.1 nm and a zeta potential of −30.26±0.12 mV;

e) cumulative CBD release at 24 hours is 50.74±2.44% at pH 6.8 and 53.99±1.4% at pH 7.4; and f) the composition is stable without precipitation for several months at 4° C.

\* \* \* \* \*